(12) United States Patent
Hanak et al.

(10) Patent No.: US 6,780,632 B1
(45) Date of Patent: Aug. 24, 2004

(54) PURIFICATION OF CELLULAR COMPONENTS THAT ARE SUBSTANTIALLY RNA FREE

(75) Inventors: Julian Alexis John Hanak, Cheshire (GB); Steven Geraint Williams, Cheshire (GB)

(73) Assignee: Cobra Biologics Limited, Newcastle (GB)

( * ) Notice: Subject to any disclaimer, the term of this patent is extended or adjusted under 35 U.S.C. 154(b) by 0 days.

(21) Appl. No.: 09/291,347

(22) Filed: Apr. 14, 1999

Related U.S. Application Data

(60) Provisional application No. 60/081,726, filed on Apr. 14, 1998.

(30) Foreign Application Priority Data

Apr. 14, 1998 (GB) .............................................. 9807922
Aug. 6, 1998 (GB) .............................................. 9817151

(51) Int. Cl.$^7$ ............................. C12N 9/22; C12Q 1/44; C07K 17/00; C07H 21/04
(52) U.S. Cl. ......................... 435/270; 435/19; 435/199; 435/41; 435/69.1; 435/72; 435/91.1; 530/350; 536/23.2
(58) Field of Search .......................... 435/199, 19, 270, 435/41, 69.1, 72, 91.1; 530/350; 536/23.2

(56) References Cited

U.S. PATENT DOCUMENTS

| | | | |
|---|---|---|---|
| 5,500,370 A | 3/1996 | Jendrisak et al. | ........ 435/320.1 |
| 5,610,066 A | 3/1997 | Fuller et al. | ............. 435/320.1 |

FOREIGN PATENT DOCUMENTS

EP   0 537 399 A1   4/1993

OTHER PUBLICATIONS

Cannistraro et al., Eur J Biochem 181:363–370, 1989.*
Meador et al., Gene 95:1–7, 1990.*
Zhu et al. J. Bacteriol. 172(6):3146–3151, 1990.*
Meador, J. et al., Gene, vol. 95, pp. 1–7, 1990.*
Sambrook, J. et al., "Molecular Cloning," Cold Spring Harbor Press, pp. 1.34, 1.38, 1.39, 1989.*
Meador, J. et al., Eur. J. Biochem., vol. 187, p. 549–553, 1990.*
Zhu, L. et al., J. Bacteriol., vol. 172, No. 6, pp. 3146–3151, Jun. 1990.*
Clare, J. et al., Gene, vol. 105, pp. 205–212, 1991.*
Kaul, M.L.H. et al., "Efficient and Rapid Method for Midi–Scale Preparation of Purified Plasmid DNA," *The Nucleas*, 1990, 33(3), 107–110.
McMaster, G.K. et al., "Rapid Purification of Covalently Closed Circular DNAs of Bacterial Plasmids and Animal Tumor Viruses," *Analyt. Biochem*, 1980, 109, 47–54.
Rubsam, L. Z. et al., "Improved method to prepare RNA–free DNA from mammalian cells," *J. Chromatography B*, 1997, 702, 61–68.
Saha, B. et al., "A New Method of Plasmid DNA Preparation by Sucrose–Mediated Detergetn Lysis from *Escherichia coli* (Gram–Negative) and *Staphylococcus aureus* (Gram–Positive)," *Analyt. Biochem.*, 1989, 176, 344–349.
Sharma, R.C. et al., "Rapid Procedure for Isolation of RNA–Free Genomic DNA from Mammalian Cells," *BioTechniques*, 1993, 14(2),176 and 178.
Summerton, J. et al., "A Rapid Method for Preparation of Bacterial Plasmids," *Analyt. Biochem.*, 1983, 133, 79–84.

* cited by examiner

Primary Examiner—Rebecca E. Prouty
Assistant Examiner—Delia Ramirez
(74) Attorney, Agent, or Firm—Cozen O'Connor, P.C.

(57) ABSTRACT

The invention relates to host cells and methods of preparing a substantially RNA-free cellular component, comprising culturing cells producing the cellular component in a medium and lysing the cells to produce a cell lysate, wherein the cell lysate contains the cellular component and sufficient RNase activity to degrade substantially all of the RNA molecules present in the cell lysate. The invention also relates to substantially RNA-free cellular components.

12 Claims, 18 Drawing Sheets

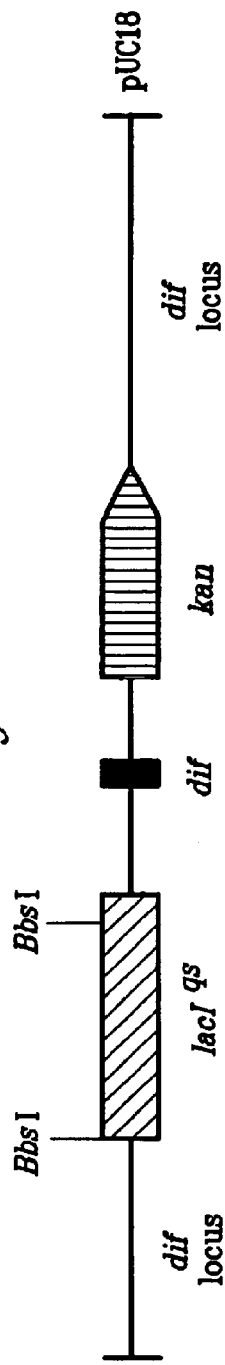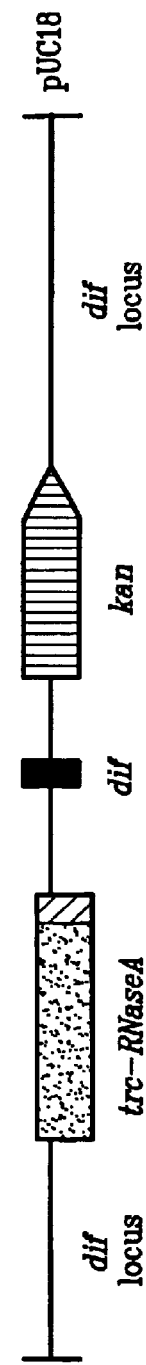
FIG. 15A
FIG. 15B

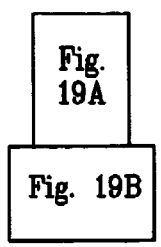
FIG. 19
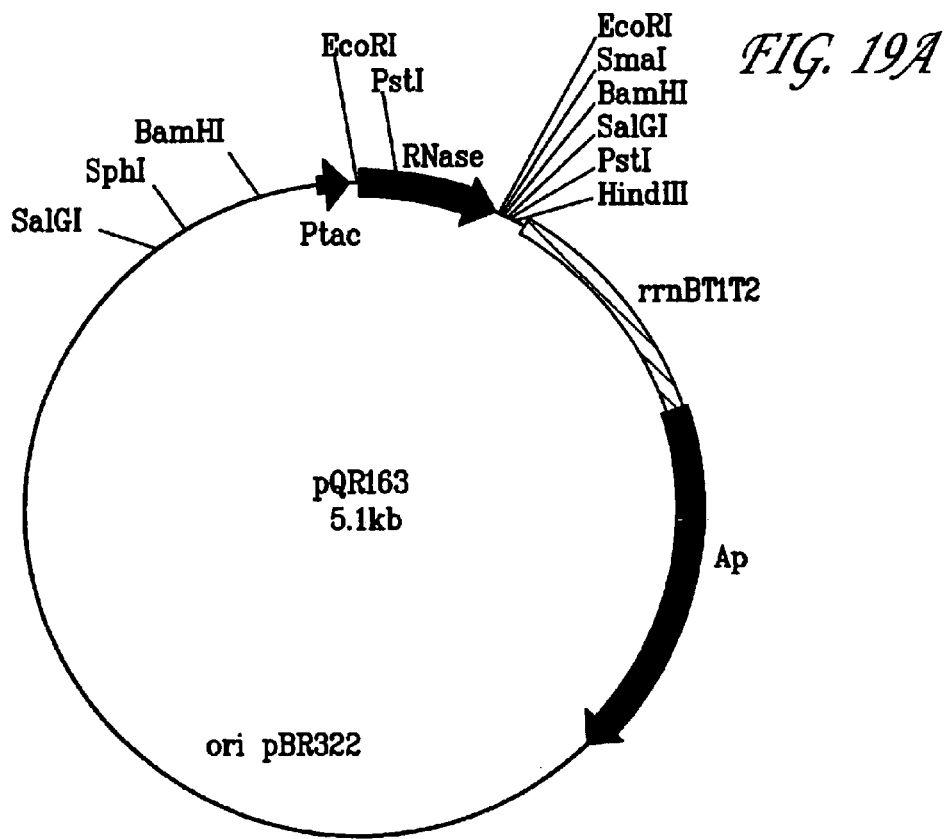
FIG. 19A
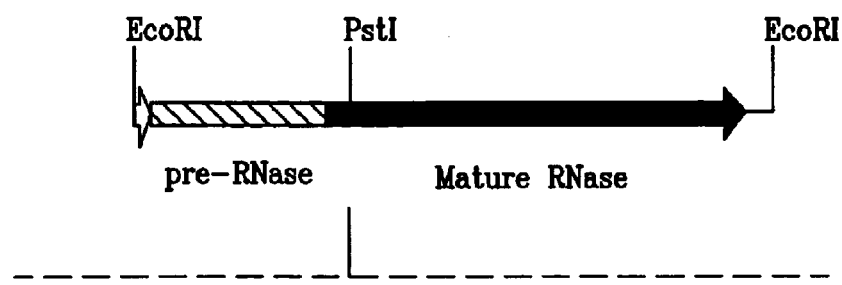

US 6,780,632 B1

PURIFICATION OF CELLULAR COMPONENTS THAT ARE SUBSTANTIALLY RNA FREE

This application claims priority under 35 U.S.C. § 119(e) to provisional application Serial No. 60/081,726, filed Apr. 14, 1998, and UK Applications 9807922.1, filed Apr. 14, 1998 and 9817151.5, filed Aug. 6, 1998, all applications hereby incorporated by reference in their entireties.

FIELD OF THE INVENTION

The invention relates to the production of RNA free cellular components, and a method of removing RNA from preparations of cellular components.

BACKGROUND OF THE INVENTION

The ribonuclease enzyme family (hereafter referred to as RNases) has been extensively studied. Numerous RNases have been characterized and the genes encoding some of these proteins have been cloned.

RNases hydrolyze one or more of the phosphodiester bonds in single stranded and double stranded RNA as well as RNA in RNA:DNA hybrids. RNases differ in their specificity for either a particular form of the RNA substrate (for example single stranded, double stranded or in a DNA:RNA hybrid) or their specific point of RNA cleavage.

One biological activity of RNase enzymes is the processing of mature molecules of RNA from precursor forms (Genes, Benjamin Lewin ed., John Wiley & Sons, 2nd edition, p.395, 1985). Certain RNases can affect the growth and differentiation of mammalian cells by virtue of an intrinsic anti-tumor activity (references within Ribo et al., Prot. Express. and Purif. 7: 253–261, 1996).

RNA is a major contaminant of preparations from cell lysates. For example, plasmid DNA preparations contain RNA that is difficult to remove by anion exchange or size exclusion chromatography because it is similar in size (with respect to exclusion by SEC matrices) and charge to DNA. RNase A hydrolyzes RNA after C and U residues by cleaving between the 3'-phosphate group of a pyrimidine ribonucleotide and the 5'-hydroxyl of the adjacent nucleotide. This enzyme is used to degrade RNA to low molecular weight species that no longer copurify with plasmid or genomic DNA. RNase I can also be used to remove RNA from preparations of plasmid or genomic DNA. RNase A is also commonly used for the enzymatic digestion of host derived RNA during the production of recombinant protein from *E. coli*.

A prior art method of removing RNA from a sample is to add a large quantity of an exogenously produced RNase. For example, to remove RNA from plasmid DNA bovine RNase A is added to a final concentration of 100 μg/ml (QIAGEN Plasmid Handbook February 1995, QIAGEN Ltd. Unit 1 Tillingbourne Court, Dorking Business Park, Dorking, Surrey RH4 1HJ, UK). Bovine RNase A is commonly used at a final concentration of approximately 10–100 μg/ml for the enzymatic digestion of host derived RNA during the production of recombinant protein from *E. coli*. A chief disadvantage of prior art methods is that the cellular component that is treated according to these methods often contains residual RNase of animal origin.

There are limitations to using exogenously produced RNases. First, it is difficult to purify large amounts of RNase from the tissue of origin. This is presumably because high concentrations of active RNase will degrade host cell RNA and impair normal cell functions to a level that can be toxic to a cell. Therefore, it is difficult to produce large quantities of active RNase by expression in cells because high concentrations of active RNase will be toxic to a cell. It is also difficult to produce large quantities of active RNase by expression in cells because RNase can be sensitive to proteases of the host in which it is being synthesized, and because RNases that are over-produced and accumulate as in e.g. *E. coli* inclusion bodies cannot always be correctly refolded. The most significant limitation to using exogenously produced RNase is that, if the exogenously added RNase is of animal origin, following RNase treatment the presence of residual enzyme can contaminate a DNA preparation, thereby rendering it unacceptable for certain applications, including gene therapy. Third, it is expensive to produce RNase in large quantities.

There is a need in the art for plasmid DNA and protein preparations that are substantially free from contaminating RNA.

There is a need in the art for methods of producing RNA-free cellular components that are suitable for administration to human subjects.

There is a need in the art for a method of removing RNA from cellular components that does not rely on incubating a cellular lysate or purified component with added exogenously produced RNase.

SUMMARY OF THE INVENTION

The invention features a method of preparing a substantially RNA-free cellular component comprising culturing cells producing the cellular component in a medium and lysing said cells to produce a cell lysate, wherein said cell lysate contains said cellular component and sufficient RNase activity to degrade substantially all of the RNA molecules present in said cell lysate.

In a preferred embodiment, the RNase is produced by cells producing the cellular component.

Alternatively, the RNase is produced by cells in the medium other than those cells producing the cellular component.

The invention also features a method of preparing a substantially RNA-free cellular component, comprising culturing and lysing cells producing the cellular component and cells producing an RNase in an amount sufficient to degrade substantially all of the RNA present in the preparation.

Preferably, the cells producing the cellular component also produce the RNase and the culture and lysate contain cells producing the cellular component and an RNase in an amount sufficient to degrade substantially all of the RNA present in the preparation. Preferably, the cellular component and the RNase are produced by the same cell.

In preferred embodiments of both of the above-described inventive methods, the cellular component is one of a DNA, a protein, and a carbohydrate. Preferably, the cellular component is one of a recombinant DNA, a recombinant protein and a recombinant carbohydrate. Preferably, the RNase is encoded on a plasmid and the cellular component is encoded on the same plasmid, another plasmid or on the cell's chromosome.

In preferred embodiments of both of the above-described inventive methods the gene encoding said RNase is integrated into the genome of the cell producing the RNase.

In some methods of the invention, it is preferred that the RNase is non-specific. Such a non-specific RNase may be RNase A, RNase M of RNase I.

In preferred embodiments of both of the above-described inventive methods, a cell producing an RNase produces the RNase in a regulated manner.

Preferably, the RNase produced by the host cell is overproduced, either by inducible production, or by constitutive production. The RNase overproduced by the host cell also may be secreted out of the host cell cytoplasm, for example, secreted into the host cell periplasm or secreted out of the host cell into the medium.

In some methods, it is preferred that the RNase is a non-specific RNase.

The invention also features a composition comprising a host cell that produces a recombinant DNA, a recombinant protein, or a recombinant carbohydrate and also produces an RNase in a regulated manner.

RNase produced in said regulated manner is overproduced, or inducibly overproduced, or constitutively overproduced. The RNase produced by the host cell also may be secreted out of the host cell cytoplasm, for example, secreted into the host cell periplasm or secreted out of the host cell into the medium.

In some methods, it is preferred that the RNase is a non-specific RNase.

The invention also features a composition comprising a host cell that produces a recombinant DNA, a recombinant protein, or a recombinant carbohydrate and a host cell that produces an RNase in a regulated manner.

RNase produced in said regulated manner is overproduced, or inducibly overproduced, or constitutively overproduced. The RNase produced by the host cell also may be secreted out of the host cell cytoplasm, for example, secreted into the host cell periplasm or secreted out of the host cell into the medium.

The invention also features a pharmaceutical composition comprising a cellular component that is substantially RNA-free, in a pharmaceutically acceptable carrier. The present invention also provides a pharmaceutical composition comprising a cellular component that is substantially RNA-free obtainable by the methods of the present invention, in a pharmaceutically acceptable carrier.

Preferably, the cellular component that is substantially RNA-free is made according the methods described herein.

As used herein, "substantially RNA-free" and "substantially all of the RNA molecules" refers to the exceedingly small amount of RNA that is permitted in a preparation of a cellular component that is useful for administration to humans. Acceptable exceedingly low levels of RNA are as follows.

"Substantially RNA-free DNA" refers to the presence in a sample containing the cellular component of less than 1%, preferably less than 0.2% and most preferably less than 0.1%–0.01% (w/w of RNA/DNA in the sample).

"Substantially RNA-free protein" refers to a protein preparation that contains less than 1% and preferably less than 0.2% and most preferably less than 0.1%–0.01% (w/w) of RNA/protein. When the protein is a therapeutic protein "substantially RNA-free protein" refers to a therapeutic protein preparation that contains less than 10 ng of RNA/dose, preferably less than 500 pg of RNA/dose, more preferably less than 100 pg of RNA/dose, most preferably less than 5–10 pg of RNA/dose.

"Substantially RNA-free carbohydrate" refers to a carbohydrate preparation that contains less than 1% and preferably less than 0.2% and most preferably less than 0.1%–0.01% (w/w) of RNA/carbohydrate.

"Cell lysate" refers to the composition produced on lysing cells wherein the composition does not comprise exogenously produced RNase. Other exogenously produced components may be added to the cell lysate such as proteases or protease inhibitors.

Preferably, the cell lysate will contain significantly less RNase protein than prior art methods where exogenous RNase is added to cell lysate. "Significantly less" in this context refers to less than 10 µg–50 µg RNase/ml lysate, preferably less than 10 µg RNase/ml of lysate and more preferably less than 1 µg RNase/ml.

As used herein, "cellular component" refers to any one of DNA, including but not limited to plasmid DNA, cosmid DNA, yac DNA, episomal DNA, or genomic DNA; recombinant protein, and recombinant carbohydrate.

As used herein, "recombinant" refers to DNA, protein or carbohydrate that is not naturally occurring in a cell or produced in an amount that is not normally produced by the cell.

As used herein, "cell" refers to any eukaryotic or prokaryotic cell. Preferred eukaryotic cells include HeLa cells, CHO cells, myeloma cell lines such as NSO, insect cells such as Sf21 and Sf9 cells, plant cells and lower eukaryotic cells including yeasts. Most preferably the term "cell" refers to a gram negative or gram positive bacteria, including but not limited to *E. coli, Salmonella typhimurium*, Bacillus spp., Streptomyces spp. and *Pseudomonas aeruginosa*.

"Regulated manner" refers to gene expression, for example, of an RNase gene in a host cell that is transcriptionally regulated, for example, constitutively or inducibly. It also refers to regulation at the level of protein production, for example, the use of a signal sequence or a fusion protein to direct a protein to the host cell periplasm or out of the host cell and into the medium surrounding the host cell.

"Inducible" or "induction" refers to transcriptional activation or derepression; "constitutive" refers to continuous transcription often at a constant level; "signal sequence" refers to an amino acid sequence that directs secretion of the protein into the periplasm or out of the cell; "secretion" refers to movement of a secreted protein out of the host cell cytoplasm and into the periplasm or host cell culture medium; "periplasm" refers to the host cell compartment between inner and outer cell membranes of, for example, *E. coli*.

"Overexpresses" or "overproduces" refers to gene expression at a level higher than that normally expressed in the host cell; "overproduced" refers to production in an amount higher than that normally produced by the cell. Thus, over-expression of a given gene or overproduction of a gene product or a recombinant DNA encompasses production of 10% or more, 50% or more, 100% or more, or even up to over 200–500% more of the gene product than the cell normally produces in the absence of the over-expressed gene.

The invention provides DNA, protein or carbohydrate preparations that are substantially free of contaminating RNA. The invention is particularly useful in providing preparations that involve administration to humans, but also for other uses, including for accurate determination of DNA concentrations by absorbance at 260 nm (where RNA also absorbs), and for investigating both DNA/RNA and DNA/protein interactions. Substantially RNA-free protein is required for therapeutic applications, for estimating protein concentrations by absorbance at 280 nm, for analysis of protein crystal structures, for studying protein/DNA and protein/RNA interactions, and for certain protein purification protocols where nucleic acid binding reduces the affinity of protein for ion-exchangers or reduces the capacity of ion-exchangers for protein.

The invention is applicable to any use requiring a preparation of a cellular component, such as DNA, protein, carbohydrate, that is substantially free of contaminating RNA, for example, for preparation of a cellular component such as DNA or a protein or a carbohydrate that is suitable for therapeutic use in humans.

Further features and advantages of the invention will become more fully apparent in the following description of the embodiments and drawings thereof, and from the claims.

BRIEF DESCRIPTION OF DRAWINGS

The drawings are briefly described.

FIG. 15 shows A) the plasmid pN1D274EkanI, which is pUC18 with a 5.2 kb region flanking the dif locus as an insert. The kan gene was inserted into an NsiI site, and lacI$^{qs}$ between two StyI sites. B) Cutting with BbsI allows removal of most of lacI$^{qs}$ and replacement by trc-RNaseA. This plasmid (pRNaseA) is linearised and used to insert trc-RNaseA into the *E. coli* chromosome by homologous recombination.

DETAILED DESCRIPTION

Figure 1:
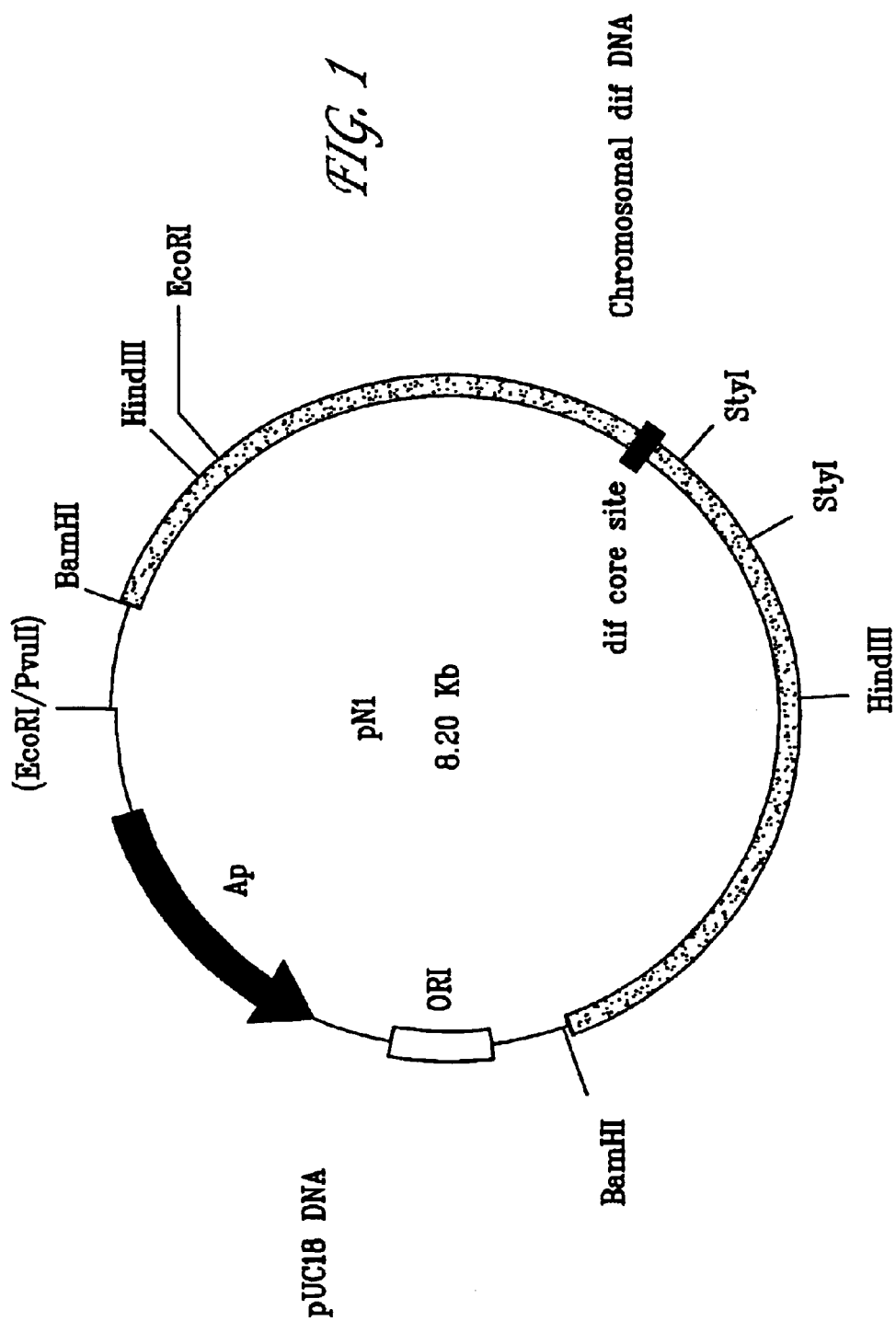
FIG. 1 shows plasmid pN1.

The invention provides for a method of producing substantially RNA-free cellular components that includes producing a selected cellular component and an RNase in the same host cell or different host cells that are co-cultured such that, upon lysis of the cell(s), sufficient RNase activity is present so as to degrade substantially all of the RNA molecules in the lysate.

The cellular component may be DNA, protein or carbohydrate that is produced according to the invention substantially RNA-free. This may be achieved, for example, using a gene encoding a cellular component that is introduced into a host cell that has been engineered to express an RNase protein, or by culturing and lysing two different host cells that individually produce the cellular component and the RNase.

RNase Genes and RNases Useful According to the Invention

Genes encoding a variety of RNase proteins have been cloned. Ideally, the RNase of the invention is non-specific (for example, bovine RNase A and *E. coli* RNase M used at high concentrations) and therefore will degrade all types of RNA molecules. Non-specific RNases hydrolyze phosphodiester bonds in single stranded or double stranded RNA or RNA/DNA molecules, anywhere along the length of the RNA molecule.

The protein products and the genes for bovine RNase A (Tarragona-Fiol et al., Gene, 118: 239–245, 1992, Schein et al., Biochem. J., 283: 137–144, 1992, Laity et al., PNAS 90: 615–619, 1993, delCardayre, Prot. Engineer. 8: 261–273, 1995, Okorokov et al., Prot. Express. Purif. 6: 472–480), and murine and rat RNase A homologs (Schein et al., supra) have been cloned and characterized.

RNase H hydrolyzes RNA molecules that are hybridized to a complementary DNA strand and is used in molecular biology to degrade the RNA strand after first-strand synthesis in the production of double-stranded cDNA. RNase H is also used to remove polyA tails from mRNA that has hybridized to oligo-dT$_{12-18}$ (described in U.S. Pat. No. 5,459,055).

RNase I cleaves the phosphodiester bond of single stranded RNA 3' of any ribonucleoside and is used for RNase protection assays, mapping and quantification of RNA and mismatch detection. *E. coli* RNase I and RNase M (Meador and Kennell, 1990, Ribo et al., Prot. Express. Purif. 7: 253–261, 1996) have been cloned, isolated and characterized.

RNase T1 preferentially cleaves 3' to G residues and is used for RNA sequence analysis and RNA fingerprinting. *Aspergillus oryzae* RNase T1 and T2 (Fujimura et al., FEBS, 265:71–74, 1990, Quass et al., Eur. J. Biochem. 173:617–622, 1988) have been cloned, isolated and characterized.

RNase4 (Seno et al., Biochim. Et Biophys. Acta, 1261: 424–426-1995) has been cloned, isolated and characterized.

Human pancreatic RNase (Russo et al, FEBS 333: 233–237, 1993) has been cloned, isolated and characterized.

*Bacillus amyloliquefaciens* BaRNase (Hartley, J. Mol. Biol. 202: 913–915, 1988) has been characterized with respect to synthesis and processing.

Expression of a Selected RNase Gene in a Host Cell

According to the invention, an RNase gene can be modified so that the RNase protein is localised in either the periplasmic space or the cellular supernatant, for example, by directing the location of the RNase using a signal sequence or by creating a fusion protein that is secreted.

Alternatively, expression of the RNase may be selectively controlled by placing the RNase gene under the control of an inducible promoter.

Alternatively, the RNase gene may be introduced into a host cell and integrated into the chromosome of the host cell.

Vectors used to overproduce RNase have been modified to minimize problems due to toxic effects of improperly folded RNase on the host cell in which the RNase is being produced, sensitivity of unfolded RNase to proteases present in the host cell and the improper refolding of some RNases that have been produced in inclusion bodies.

Integration of an RNase Gene into the Chromosome of the *E. coli* Host Strain The following methods may be used to provide a host cell containing an RNase gene integrated into the host cell chromosome.

1. Cloning RNase A into pN1

The RNase A gene was isolated from the expression vector pQR163 (Tarragona-Fiol et al., supra) by PCR (Current Protocols in Molecular Biology, Ausubel, F. M et al. eds., John Wiley & Sons Inc.) using the primers

5'-CTCGAATTCAATGTTCTTGGAGGATGATTG-3'
     SEQ ID NO:1

5'-TACGAATTCGGCCTTAGGTAGAGACCTAC-3'
     SEQ ID NO:2.

The isolated RNase gene was inserted into the EcoRI site of pUC18 such that an inframe fusion was created between the lacZ gene and the hexapeptide located 5' to the RNase A gene. The expression of the RNase A gene and the hexapeptide was controlled by the lacZ promoter. The LacZ-RNase A construct was then excised by a Hae II digest, blunt ended, and inserted into pN1 (FIG. 1) previously digested with Sty I and blunt ended.

The resulting construct is referred to as pN1RNase A.

2. Introduction of pN1RNase into *E. coli*

The resulting construct, referred to as pN1RNase A, consists of an RNase expression cassette flanked on both sides by the *E. coli* dif locus containing chromosomal DNA homology. The dif locus is a 28 base pair region that comprises the recognition site for XerC and XerD recombinases (Hayes and Sherratt, J. Mol. Biol., 266: 525–537, 1997, Kuempel, et al., The New Biologist 3: 799–811, 1991).

The resultant pN1RNase A construct was used, to shuttle the RNase A gene cassette into the *E. coli* strains JC7623 and then DH1 by the following method.

pN1RNase A was linearized with Sal I (or another suitable restriction enzyme), or subjected to a partial digest reaction with Sal I. The resulting fragment (containing the excised but intact RNase expression cassette) was used to transform calcium-competent JC7623 cells (recB21, sbcC201, recC22, sbcB15; Horii and Clark, J. Mol. Biol. 80: 327–344, 1973, Lloyd and Buckman, J. Bacteriol. 164: 836–844, 1985) by linear transformation as described by Winans et al., J. Bacteriol. 161:1291–1221, 1985 and Jasin and Schimmel, J. Bacteriol. 159: 783–786, 1984.

Figure 2:
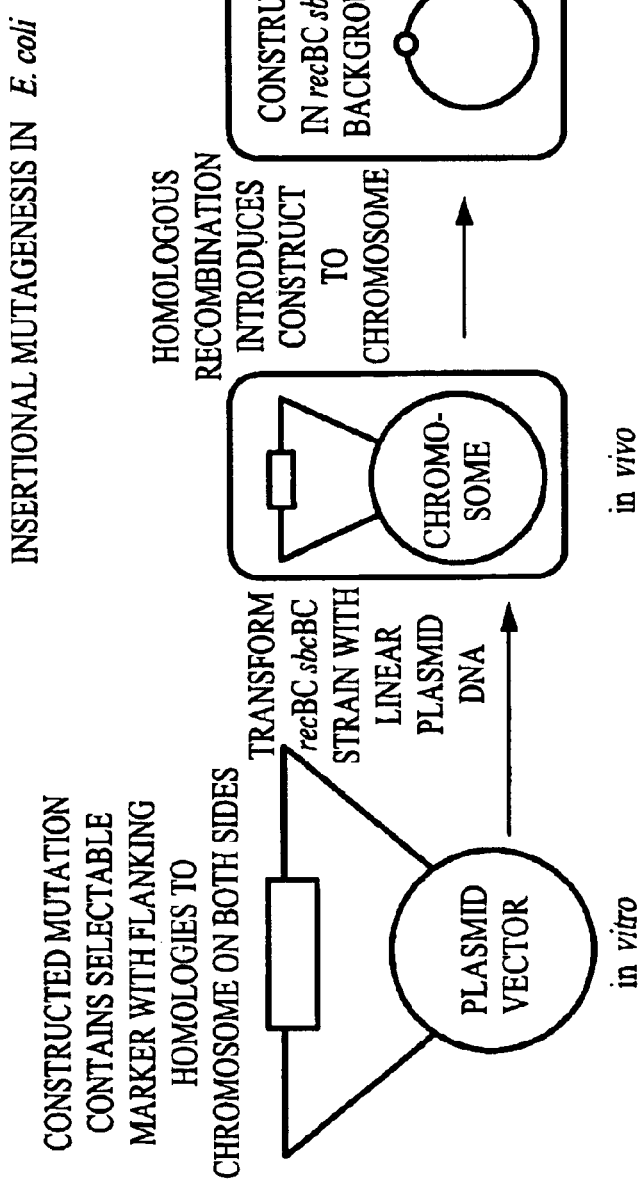
FIG. 2 is a diagrammatic representation of the strategy for introducing and deleting plasmid DNA into the *E. coli* chromosome and for deleting chromosomal DNA from the *E. coli* chromosome by insertional mutagenesis and homologous recombination.

P1 phage transduction was then used to move this chromosomal construct into the dif locus of *E. coli* DH1 (F-, supE44, recA1, endA1, gyrA96, thi-, hsdr17, relA1 as described in Hanahan, Mol. Biol. 166: 557–580, 1983, and Bachmann, in *Escherichia coli* and *Salmonella typhimurium*, Cellular and Molecular Biology, ed. Neidhardt, F. C. Et al., ASM, pp. 1190–1219, 1987) or another suitable DNA vector host strain as detailed in FIG. 2. To facilitate integration of the RNase gene into the host cell chromosome, the target host strain was first rendered transiently RecA+ by transformation with the unstable, recA-containing plasmid pPE13 (Hickson et al., *Escherichia coli* Mol. Gen. Genet, 184: 68–72, 1981). Transformation of the host strain with pPE13 was performed using the calcium phosphate method of preparing competent cells, as described in Short Protocols in Molecular Biology, Ausubel et al., eds, Wiley, 3rd edition, 1993).

3. PCR Amplification of pN1RNase I

The RNase I gene was amplified from the *E. coli* strain DH1 by PCR using the primers, 5' GGTCCTGGGGTGA TTATTTACGGCTGTGGC-3' SEQ ID NO:3, and 5'-GTTTAACTCACATGATGATACTGACTGTTG-3' SEQ ID NO:4, and cloned into the TA cloning vector pCR3.1 (INVITROGEN) to generate pCR3.1 RNase I.

The RNase I gene was then amplified from pCR3.1RNase I by PCR using the primers, 5'-TCCAGAATTCCATGAAAGCATTCTGGGG-3' SEQ ID NO:5 and 5'-GTTGAATTCACATGATGATACTGACT GTTG-3' SEQ ID NO:6, (according to the method of Ausubel et al., Current Protocols, supra) and cloned into the EcoRI site of pUC18 such that the RNase I gene was fused in frame to the remaining sequences of the lacZ gene.

The resulting plasmid comprised an RNase I gene under the control of the lacZ promoter wherein the expression of the RNase I gene was increased in the presence of 0.5 mM IPTG. The LacZ-RNase I construct was then excised by a Hae II digest, blunt ended, and inserted into pN1 which had been digested with Sty I and blunt ended. The resulting pN1RNaseI construct was used, as above, to shuttle the RNaseI gene cassette into the *E. coli* strains JC7623 and then DH1, as above.

Integration of an RNase Gene into the Chromosome of Other Cell Types

1. Production of Cellular Components in Other Cell Types
    1.1. *S. typhimurium*.

An RNase gene may be inserted into the chromosome of *S. typhimurium* as described in Bachmann et al., 1977, in *E. coli* and *Salmonella typhimurium*, Cellular and Molecular Biology, ed. Neidhardt et al., ASM, or as described in Nakayama et al., Bio/Technology, 6: 693–697, 1988).

2. Production of Recombinant Protein in Other Cell Types
    2.1. Bacillus spp.

An RNase gene may be inserted into the chromosome of Bacillus spp. as described in Solma et al., J. Bact., 173: 6889–6895.

2.2. Streptomyces spp.

An RNase gene may be inserted into the chromosome of Streptomyces spp. as described in Chapter 6 in Plasmids A practical Approach (2nd edition) Edited by K. G. Hardy or as described in Motamedi et al., Gene, 160:25–31, 1995.

Integrative expression vectors for heterologous expression of genes in Streptomyces have been developed. The vectors are comprised of a strong constitutive promoter, $P_E$, a synthetic ribosome-binding site, ATG start codon, multiple cloning site, transcription terminator and hygromycin-resistance-encoding gene ($Hy^R$). The vectors also contain a ColE1 replicon for propagation in *Escherichia coli* and a wide-host-range Streptomyces integration element, the mini-circle, to direct the insertion of the vectors into the Streptomyces genome at the mini-circle attachment site. $Hy^R$ transformants are stable in the absence of drug selection. Conjugative derivatives can be constructed by incorporating oriT, the origin of transfer of the IncP plasmid RK2, into these vectors, and conjugal transfer from an appropriate *E. coli* donor to *Streptomyces lividans* (*Sl*) can be done. Derivatives of these vectors potentially useful for gene disruption, as well as complementation, have also been described. It has been demonstrated that replicative forms of the constructed mini-circle-based vectors in *Sl*, can co-exist with the integrated copy of the vector, without any apparent instability problems. The utility of these vectors has been demonstrated by expression of the gene encoding 31-O-methyltransferase, which is involved in methylation at position 31 of the immunosuppressive drug FK506 in *Sl* (Motamedi et al., Supra).

2.3. Pseudomonas spp.

An RNase gene may be inserted into the chromosome of Pseudomonas spp. as described in Gene replacement in *Pseudomonas aeruginosa* in Methods in Enzymology, 235: 466–474 1994, Molecular Microbiology, 6:1195–1204, 1992 or as described in Schweizer and Hoang, Gene, 158: 15–22, 1995).

A novel pUC19-based gene replacement vector has been developed. This vector incorporates (i) the counterselectable sacB marker, (ii) a lacZα allele for blue-white screening, (iii) an oriT for conjugation-mediated plasmid transfer and (iv) unique cloning sites for SmaI and the rare-cutting meganuclease I-SceI. These rare restriction sites are also present on the helper plasmid pUC19Sce. The replacement vector is engineered to contain few restriction sites to gain greater access to restriction sites within cloned DNA fragments, thus facilitating their genetic manipulation. The usefulness of the system was demonstrated by chromosomal integration of a newly constructed xylE::$Gm^R$ fusion cassette into the glpD gene of *Pseudomonas aeruginosa* (Schweizer and Hoang, supra).

Preparation of Cells Expressing RNase and Recombinant DNA or Protein

Cells which express an RNase gene and a DNA or protein of interest are prepared as follows.

*E. coli* host strains DH1, DH5α, DH10B, JM109, DL795, XL1-BLUE and TG1 can be used for production of recombinant plasmid DNA, and *E. coli* strains BL21(DE3), JM109 (DE3) and HB101 can be used for the production of recombinant protein.

1. Curing *E. coli* of Rec A Containing Plasmid

Following integration of the heterologous RNase expression cassette into the chromosome of the DNA vector host strain as described in the section entitled introduction of pN1RNase into *E. coli*, the host cells will be 'cured' of the recA-containing plasmid pPE13 by one of the following methods: serial subculture in the absence of the selectable marker drug encoded for by the plasmid (e.g. selection in the absence of ampicillin), titration with DNA intercalators such as ethidium bromide, or growth in 10% SDS (Tolmasky et al., Virulence plasmids. In Plasmids: a practical approach, Ed. K. G. Hardy, IRL Press Oxford, UK, 1993). Plasmid free segregants will be selected by replica plating (plus and minus selection), and 'curing' will be confirmed by a rapid procedure for the screening of recombinant plasmid DNA (Birnboim and Doly, Nucleic Acids Res. 7: 1513–1523, 1979).

2. Transformation of *E. coli* with Recombinant Plasmid

Once cured the host cells will be made competent for DNA transformation, transformed with the recombinant plasmid (Sheen, p. 1.8.5, in Ausubel, Current Protocols, supra) and selected under the appropriate conditions.

3. Purification of Recombinant DNA or Protein

Recombinant Plasmid DNA

For production of recombinant plasmid DNA, the transformed clones will be used directly to propagate plasmid DNA. Plasmid DNA is prepared according to procedures well-known in the art. See, for example, Birnboim and Doly, supra, Tolmasky et al., supra, and Ausubel, Current Protocols, supra).

Plasmid DNA can be prepared as described in WO 97/29190 except that the step of adding an exogenous RNase is omitted. Alternatively, the plasmid DNA can be prepared according to the method of Horn et al., (Human Gene Therapy, 6: 565–573, 1995).

Production of Bacterial Culture

Fermentation in complete TB medium containing the appropriate concentration of antibiotic for selection (e.g.50 μg/ml kanamycin for kan selected plasmids) will be performed in a 10-liter BRAUN BIOSTAT ED fermenter. Fermentation conditions will be maintained as follows: Temperature will be controlled at 30° C., agitation at 600 rpm, airflow at 10 liters/min, and pH at 7.0. Bacteria will be harvested in late log phase (10–11 hr post inoculation) at a final $OD_{600}$ of approximately 30 in a JOUAN centrifuge at 3,000×g for 30 min and stored at −20° C. A 0.75-ml aliquot will be withdrawn at harvest and processed for miniprep analyses (PROMEGA WIZARD, Madison, Wis.). According to this method, the average fermentation should yield 4 mg of plasmid DNA/liter (Horn et al., supra).

Lysis and Plasmid Recovery

Fresh or frozen bacteria will be lysed using a modification of the standard alkaline method. The yield should be equivalent from fresh and frozen cell paste. Approximately 180 grams of bacteria will be resuspended in 1.4 liters of 61 mM glucose, 10 mM Tris, 50 nM EDTA pH 8.0 buffer prechilled to 4–10° C. Lysis will occur after the addition of 2.8 liters of 0.2 N NaOH, 1% SDS buffer prechilled to 4–10° C. followed by incubation on ice for 10 min. Cellular debris will be precipitated with the addition of 2.1 liters of 3 M potassium acetate pH 5.0 prechilled to 4–10° C., followed by incubation on ice for 10 min. Cellular debris in the lysate will be removed by filtration through MIRACLOTH (CALBIOCHEM, San Diego, Calif.). Once the cell debris has been removed, the lysate will be poured twice through a minimum of 16 layers of MIRACLOTH each pass. Plasmid DNA will be precipitated from the cleared lysate by the addition of 0.6 volumes of −20° C. 2-propanol followed by incubation for 1–2 hr at room temperature. Approximately 4.6 liters of the clear liquid layer above the enriched plasmid precipitate will be decanted. The concentrated plasmid DNA precipitate at the bottom of the vessel will be transferred to 250-ml centrifuge bottles and centrifuged at 10,000×g for 30 min in a GSA rotor and SORVALL RC5B centrifuge. Supernatants from the centrifugation will be discarded and the pellets will be drained and resuspended in approximately 200 ml of 10 mM Tris, 1 mM EDTA pH 8.0 (TE buffer). Solid ammonium acetate will be dissolved in the plasmid DNA solution with stirring to a final concentration of 2.5 M. The ammonium acetate solution containing the plasmid DNA will then be incubated on ice for 15 min. The resulting precipitate was removed by centrifuging at 10,000×g for 20 min as described above. The supernatant will be filtered through a 0.8 μm nitrocellulose disposable membrane filter bottle unit (THE NALGE COMPANY, Rochester, N.Y.) and sufficient 30% PEG-8000 in 1.6 M NaCl will be added to achieve a final concentration of 10% PEG-8000 (Lis and Schleif, 1975; Lis, 1980). Plasmid DNA will be allowed to precipitate from this solution for 8–24 hr at 4° C. Plasmid DNA will be collected by centrifuging at 10,000×g for 30 min as described above. The pellet containing the plasmid will be resuspended in 10 ml of column buffer (10 mM Tris, 1 mM EDTA, 150 mM NaCl, pH 8.0). The plasmid will then be filtered and applied directly to the column as described below.

PHARMACIA SEPHACRYL S-1000 SUPERFINE Gel Filtration Chromatography

Two PHARMACIA XK26/100 columns will be pressure-packed, using a PHARMACIA FPLC system according to the manufacture's instructions for this support, to final bed heights of approximately 85 cm each, resulting in a total column volume of approximately 900 ml. The running buffer will be 10 mM Tris, 1 mM EDTA, 150 mM NaCl, pH 8.0. The flow rate will be 0.75 ml/min. Partially purified plasmid DNA from the PEG-8000 precipitation described above will be passed through a 0.1- to 0.22-μm sterile cellulose acetate ACRODISC syringe filter (GELMAN, Ann Arbor, Mich.) and loaded onto the column. Column operation and fraction collection will be automated with a PHARMACIA FPLC. Five-milliliter fractions will be collected in 15-ml disposable conical tubes. Following chromatography, the column and FPLC will be sanitized with 2 column volumes of 0.2 M NaOH. Fractions will be analyzed with 0.8% agarose gel electrophoresis, and fractions containing predominantly supercoiled plasmid DNA will be pooled in sterile disposable centrifuge bottles; the pool will be precipitated with two volumes of cold ethanol.

Production of Sterile Bulk Plasmid DNA

The ethanol-precipitated column-purified plasmid DNA will be collected by centrifugation at 10,000×g for 30 min. The plasmid pellet will be drained and air-dried under aseptic conditions in a laminar flow hood. The dried pellets will be resuspended in Lactated Ringer's (BAXTER, Deerfield, Ill.) and diluted to an appropriate concentration for the intended dosage. The resulting solution will be subjected to a sterilizing filtration through a pyrogen-free 0.2-μ ACRODISC filter (GELMAN, Ann Arbor, Mich.). The sterile bulk plasmid DNA will be aliquoted and stored frozen at −70° C. (Horn et al., supra).

Recombinant Protein

For the production of recombinant protein, the transformed plasmid will comprise an expression cassette for the production (overexpression) of a recombinant (usually heterologous) protein. A less preferred method for the production of protein will involve transforming an unmodified host strain with a single plasmid co-expressing RNase and the recombinant protein.

RNA may be removed from a protein preparation as follows. Polyethylenimine, a polycation which binds strongly to nucleic acids to form a precipitate can be added to a clarified cell lysate containing 10 mg/ml protein in 0.1M Tris-HCl, pH 8 at 4° C. The precipitate is removed by centrifugation (Brewer, S. J. and Sassenfeld, H. M. Engineering proteins for purification. In Protein purification applications: a practical approach, E. Harris and S. Angal eds., IRL Press Oxford, UK, 1990). It should be noted that the terms clarified lysate and cleared lysate are used interchangeably throughout this specification to refer to a cleared and clarified lysate (CL).

RNA may be removed from a cellular component such as protein using diatomaceous earth as described by Horn et al. (U.S. Pat. No. 5,576,196).

Protein is purified from a host cell preparation according to a protein purification procedure specific for the protein of interest and as known in the art. Methods for protein purification are described in Protein Purification; Principles and Practice, R. Scopes, ed., C. R. Cantor, Springer-Verlag, 1985). In general, such protein purification procedures will include the steps of culturing a host cell containing the protein expression vector, inducing protein expression, and extracting and purifying the protein of interest. For example, metal chelate chromatography can be used to purify Influenza Nuclear protein that has been tagged with histidine residues (described in Example V).

Host cells other than *E. coli* can be transformed with an RNase gene and a gene of interest by the method of PEG transformation as described in PEG Transformation of Streptomyces: Wohlleben & Moth in Chapter 6 of Plasmids; A practical Approach (supra). Host cells other than *E. coli* may also be transformed with an RNase gene and a gene of interest by the method of electroporation transformation as described in Electroporation Transformation of gram positive bacteria, Alonso & Espinosa, in Chapter 2 of Plasmids; A Practical Approach, (supra).

Regulated RNase Gene Expression

To reduce the toxic affects of RNase on the host cell, the RNase gene can be expressed under the control of an inducible promoter.

Inducible promoters that have been used to regulate the activity of RNase in *E. coli* include trp, T7, Ptac and the $P_R$ and $P_L$ promoters of phage lambda.

Method for Inducing RNase Expression in the Cytoplasm

The expression of the RNase gene may be regulated by an inducible promoter that allows only minimal expression of the RNase gene under uninduced conditions so as to prevent toxic effects of RNase during the period of uninduced growth.

A variety of inducible promoter systems can be used to regulate RNase according to the method of the claimed invention. Many of the promoters (described above) can be manipulated so that expression of the RNase gene is either increased or decreased.

To inducibly express RNase in the cytoplasm RNase expression will be induced 1–3 hours prior to the harvesting of the cells producing the cellular component of interest to allow intracellular RNA degradation to occur.

The duration of the induction period as well as the period during which RNase is expressed will be optimized to allow maximum degradation of RNA to occur without adversely effecting product quality or cellular integrity. This will be done by incubating cells expressing RNase for 5 min to 2 hours, at 4°–37° or 42° C., if induction by temperature is being employed, at a pH of 5–8 or, in the case of RNase A, a pH of 5–10. For example, if the cellular component being produced is a recombinant plasmid, conditions will be modified to avoid lysing the cells as a result of over expression of intracellular RNase.

Upon completion of RNA degradation (determined as described below), cells will be lysed and the cellular component will be purified (described below).

RNase Gene Under Control of an Inducible Promoter

The toxic affects of RNase have also been reduced by expressing the RNase gene under the control of an inducible promoter. Inducible promoters that have been used to regulate the activity of the RNase gene include trp, T7, trc, lac, $P_{tac}$ and the $P_R$ and $P_L$ promoters of phage lambda in *E. coli* (Fujimura et al., supra, Schein et al., supra, Laity et al., supra, Quaas et al., supra, Ribo et al., supra, DelCardayre et al., supra, Okorokov et al., supra, McGeehan and Brenner, et al., supra, Tarragona-Fiol et al., supra). By using an inducible promoter to regulate the expression of the RNase gene, the level of RNase protein can be maintained at a low level under non-inducing conditions.

1. Trp Promoter

A vector containing an RNase gene under the control of a trp promoter can be constructed according to the methods of Fujimura et al., supra and Schein et al., supra. Briefly, the pGH-L9 vector containing the trp promoter and the hGH (human growth hormone) gene will be digested with ClaI and SalI. The linearized vector containing the trp promoter will be isolated from a 1% agarose gel after electrophoresis. An RNase gene will be excised from a vector by digestion with ClaI and SalI or amplified by PCR, using 5' and 3' RNase specific primers that contain a ClaI or a Sal I site on the 5' end, respectively. The DNA fragment containing the RNase gene will be isolated from a 5% polyacrylamide gel after electrophoresis. The trp promoter-containing vector and the RNase gene will be mixed and incubated with T4 DNA ligase, and the desired plasmid will be obtained from *E. coli* HB101 transformants by standard procedures (Fujimura et al., supra).

2. T7 Promoter

The RNase gene can be cloned downstream of the T7 promoter (from φ10). Expression of T7 RNA polymerase will be controlled by an inducible promoter such as the lacUV5 promoter from *E. coli* BL21 (Neubauer and Hofmann, supra) or the λPL promoter in conjunction with the cI857 temperature sensitive repressor (Tabor and Richardson, supra).

The lacUV5 system is based on the lacUV5-controlled expression of the T7-RNA polymerase. The RNase gene can be cloned behind the strong φ10 promoter of the T7 phage, which is only transcribed by the T7-specific RNA polymerase (Neubauer and Hofmann, supra). This system can be utilized to regulate the expression of an RNase gene by the T7 promoter according to the following method of Neubauer et al., Appl. Microbiol. Biotechnol., 36: 739–744, 1992.

*Escherichia coli* BL21 (F- hsdS gal omp T $r_B$- $m_B$-) carrying the lambda derivative DE3 in the chromosome DNA on which was cloned the T7 RNA polymerase gene under $P_{lac}$ control and the plasmid plysS. A BamH1-Alu1 fragment containing an RNase gene can be cloned into the BamH1-AluI digested plasmid pET3, behind the φ10 promoter of the T7 phage.

This promoter has only a recognition site for the T7 RNA polymerase. Therefore the expression of the RNase gene should be very low under restrictive conditions. However, after induction of the T7 RNA polymerase synthesis by IPTG (SIGMA, St. Louis, Mo., USA) the RNase gene should be expressed very strongly (Neubauer et al. supra).

The RNase gene can be regulated by the λPL promoter in conjunction with the cI857 temperature sensitive repressor according to the method described in Tabor and Richardson, supra.

The expression of an RNase gene can be regulated in a system that utilizes the cloned T7 Gene 1 and a T7 RNA Polymerase Promoter. The expression system consists of two compatible plasmids, pGP1-2 and pT7-1. PGP1-2, a derivative of pACYC177, provides for expression of T7 RNA polymerase. PGP1-2 consists of gene 1 of phage T7 under the control of inducible $\lambda P_L$ promoter, and the gene for the heat-sensitive λ repressor, cI857.

To express a given gene, the gene is inserted into the second plasmid, pT7-1. PT7-1 contains a T7 RNA polymerase promoter, φ10, isolated from a 40-bp T7 fragment. A polylinker containing eight different restriction sites lies adjacent to the promoter to facilitate the insertion of DNA fragments. Transcription from the φ10 promoter results in expression of the cloned gene and the β-lactamase gene. Exclusive expression of these genes is achieved, after heat induction of T7 RNA polymerase, by the addition of rifampicin to shut off E. coli RNA polymerase transcription (Tabor and Richardson, supra).

A vector containing an RNase gene under the control of a T7 promoter can also be constructed according to the method of Okorokov et al., supra, Laity et al., supra, delCardayre et al., supra and Ribo et al., supra.

Briefly, the expression vector pET21d(+) can be used for the insertion of an RNase A gene in conjunction with the bacteriophage DE3 lysogen strain BL21(DE3) E. coli, which has the T7 RNA polymerase gene under control of the lac UV5 promoter inserted into the chromosome. The BamHI-HindIII fragment of pUCBFRA, with the RNase A coding sequence can be recloned into the pET21d(+) vector. To keep the open reading frame, a 19-bp NcoI-BamHI fragment from the multiple cloning site of pTZ19RJL1 will be inserted in the corresponding unique sites. This method has been used by Okorokov et al. to construct the plasmid pETFRA (Okorokov et al., supra). This method can also be used to produce a vector containing other RNase genes under the control of a T7 promoter.

3. tac Promoter

A vector containing an RNase gene under the control of a ptac promoter is constructed according to the following methods of Tarragona-Fiol et al. Supra.

Primers complementary to the 5' and 3' ends of the coding sequence for an RNase precursor can be synthesized and used for a PCR amplification. The 5' primer (primer 10) will contain additional sequence information which will incorporate a short ORF in front of the RNase precursor and an EcoRI restriction site with four additional nt to ensure correct cleavage. The 3' primer (primer 11) will contain the termination codon for RNase, an EcoRI site and an additional 4 nt to ensure correct cleavage.

The two-cistron fragment resulting from PCR amplification using these primers will contain two sets of coding sequences: one for a hexapeptide and the other for an RNase precursor. Transcription of this fragment will produce bicistronic mRNA which upon translation generates a hexapeptide and the pre-RNase.

Figure 7:
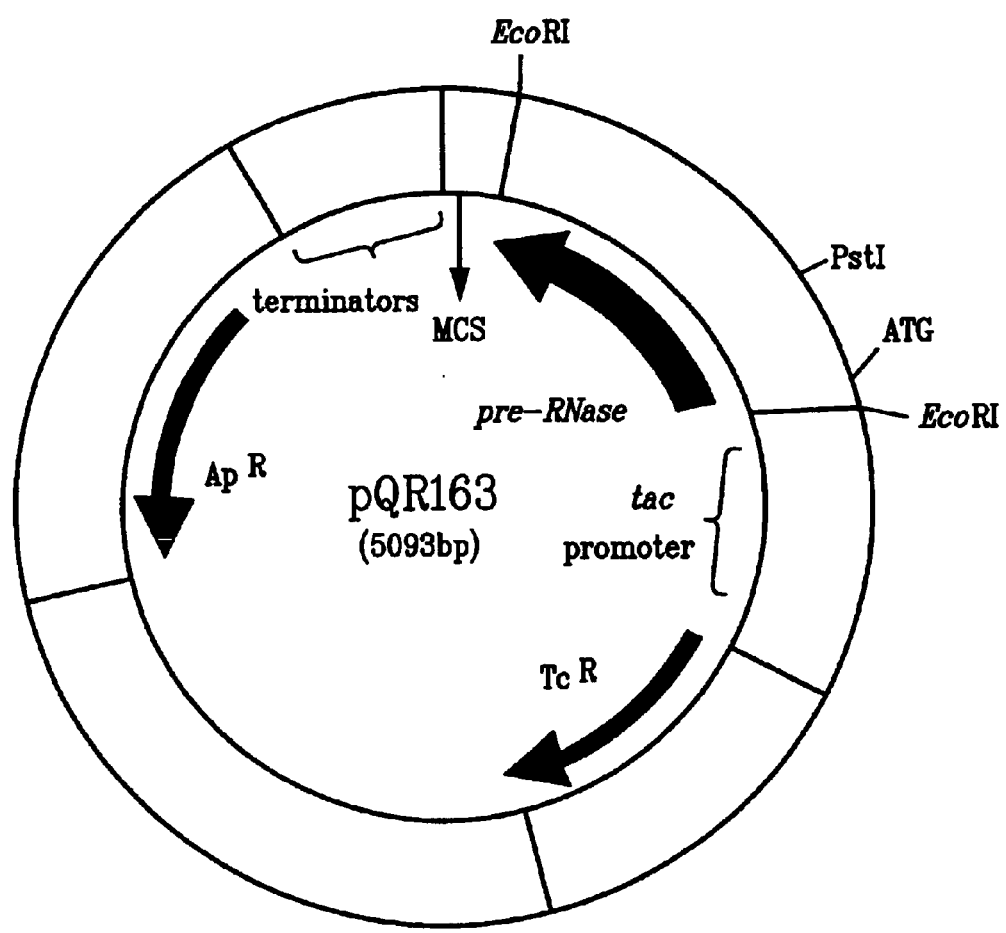
FIG. 7 shows the biscistronic recombinant plasmid pQR163 based on the expression vector pKK223.3, and coding for a hexapeptide and RNase precursor under control of the tac promoter and displaying resistance to Ampicillin and Tetracycline.

The PCR reaction will contain pQR138 as template (100 ng)/primers 10 and 11 (50 pmole/each)/all four dNTPs (0.2 mM each)/20 mM Tris-HCl pH 8.0/15 mM $(NH_4)_2SO_4$/2 mM $Mg_2Cl$/0.05% NP40/0.05% Tween 20, in a total volume of 50 or 100 μl. The reaction components will be rapidly mixed followed by centrifugation at 10,000×g (average) for 2 s at room temperature. An equal volume of paraffin oil will be added to avoid evaporation during the reaction. Template DNA will be fully denatured by incubation for 5 min at 92° C. for 1.5 min, annealing at 55° C. for 1 min, and extension at 72° C. for 1.5 min The plasmid pQR163 (see FIG. 7) contains two ribosome binding sites, one provided by the tac promoter of the vector and the other, for translation of the second cistron, is contained within the coding sequence of the first cistron. The mRNA produced upon IPTG induction of E. coli cells harboring pQR163 is bicistronic and starts from the tac promoter. The first cistron encodes a 6-amino acid peptide (Met-Phe-Leu-Glu-Asp-Asp). The stop codon of the first cistron and the start codon of the second cistron overlap such that ribosomes will continue translation of the mRNA and produce pre-RNase (Tarragona-Fiol et al., supra).

According to the method of Tarragona-Fiol, the endogenous RNase signal sequence is present in the RNase expression vector. However, other signal sequences can be cloned onto the RNase gene, as described below:

If the endogenous signal sequence is present, the synthesized precursor form of RNase will be translocated to the periplasm. N-terminal sequencing will be used to show that the signal sequence has been correctly cleaved. The oxidative environment of the periplasm will allow the correct folding of RNase to form the native enzyme as evidenced by the recovery of fully active enzyme (Tarragona-Fiol et al., supra).

4. $P_R$ and $P_L$ Promoters of Phage Lambda

A vector containing an RNase gene under the control of the $P_R$ promoter of phage lambda is constructed according to the following method of Okorokov et al. Supra.

The $P_R$ expression cassette can be isolated from the vector pCQV2 containing the $P_R$ promoter of the E. coli λ phage under cI repressor regulation. The cassette is surrounded by an EcoRI restriction site downstream of the cI coding frame and a BamHI site downstream of the $P_R$ promoter.

RNase genes can be isolated from a vector by using appropriate restriction enzymes that are compatible with pCQV2. The RNase gene can be cloned under the control of the $P_R$ promoter in the absence of a signal sequence. RNase genes can also be isolated from a vector by PCR using primers that produce an amplified fragment that contains the RNase gene and has the appropriate restriction sites on the ends.

A vector that can be used to clone the expression cassette fragment containing the RNase A gene is pUC19. The fragments EcoRI-BamHI from pCQV2 and BamHI-HindIII from pUCBFRA, containing the phoA signal peptide-RNase A fusion frame, can be joined with pUC19, restricted with EcoRI/HindIII, in a three-component ligation reaction. This method has been used by Okorokov et al., supra to construct the plasmid pEXFRA.

A vector containing an RNase gene under the control of the $P_L$ promoter of phage lambda is constructed according to the following method of McGeehan and Breener, supra The gene for RNase can be cloned in vector pN1, and transferred into plasmid pAL181, together with a linker containing the methionine start codon. In this plasmid, the RNase gene will begin just after the Shine Dalgarno sequence in pAL181.

5. Lac Promoter

A vector containing a gene regulated by the lac operator/promoter in conjunction with the lac repressor may be constructed as described in the section entitled cloning RNase into pN1 or according to Neubauer and Hofmann, supra.

A vector containing an RNase gene under the control of the lac operator/promoter is constructed according to the following method of Quass et al. supra.

pIN-III-ompA2 will be digested with HindIII and EcoRI. An RNase gene digested with the same enzymes can be inserted into pIN-III-ompA2. Since the entire gene is under the control of the lpp promoter and the lac promoter-operator, gene expression is regulated by the lac repressor, i.e. inducible by adding isopropyl-β-D-thiogalactoside.

This method has been used by Quass et al. to produce the plasmid pA2T1-1 in which the RNase $T_1$ gene is fused in frame to the ompA signal peptide gene. However, the lac promoter can also be used to regulate the expression of an RNase gene fused in frame to a variety of signal sequences (described below).

6. Trc Promoter

A vector containing an RNase gene under the control of the trc promoter is constructed according to the method of Okorokov et al. supra.

An expression vector, which provides the strong inducible trc promoter, is pKK233-2. PKK233-2 features the lacZ ribosome binding site and an ATG initiation codon, which is accessible by cleavage at the unique NcoI restriction site. The multiple cloning site is followed by the gene encoding for 5S rRNA and the strong transcription signals T1 and T2 of rrnB *E. coli* (Okorokov et al. supra). An RNase gene can be isolated from a vector by digestion with enzymes that are compatible with the multiple cloning site of pKK233-2. Alternatively, an RNase gene can be amplified by PCR using primers that direct the synthesis of a fragment that has restriction enzyme sites that are compatible with the multiple cloning site of pKK233-2.

Inducible Promoters Systems

1. Temperature Inducible Promoters

The $P_L$ promoter can be used in conjunction with the cI8571 repressor to regulate the expression of the RNase gene.

A vector expressing an RNase gene under the control of the $P_L$ promoter can be produced as described in the section entitled RNase gene under control of an inducible promoter.

Induction

The cI8571 repressor is temperature sensitive and represses gene expression at 30° C. When the temperature is increased to 42° C., the repressor is inactivated and expression occurs (Tabor and Richardson, supra).

Induction can be carried out according to the following method of McGeehan et al., supra. LB medium (50 ml) containing ampicillin (125 µg/ml) will be inoculated with a fresh colony formed from the growth of *E. coli* transformed with a vector comprising an RNase gene under the control of the $P_L$ promoter, and then grown to density overnight. This culture will be used to inoculate four 5 L Erlenmeyer flasks each containing 1 liter of LB/amp (100 mg/ml) medium. These cultures will be grown at 30° C. to an $A_{550}$ value of 1.2 in a shaker. The flasks will be transferred to a shaker warmed to 42° C., and LB medium (400 ml) preheated to 72° C. will be added to each flask to bring the temperature of each quickly to 42° C. Shaking will be continued for 25 min, and the cells will be recovered by centrifugation (10 min at 4000×g). The bacterial paste will be resuspended in 10×(v/w) denaturing buffer (8 M urea, 40 mM sarcosine, 20 mM Tris, 30 mM mercaptoethanol, 1 mM EDTA, pH 7.8). The suspension will be passed through a French press (4000 lb/inch$^2$) and the insoluble materials removed by centrifugation for 10 min at 15000×g. The clarified material will be dialyzed ($M_r$>3500 cut-off) with two changes of refolding buffer (100 mM NaCl, 50 mM Tris, 4 mM oxidized glutathione, 4 mM reduced glutathione, 1 mM EDTA, 0.4 mM phenylmethylsulfonyl fluoride (PMSF), 0.02% NaN$_3$, pH 7.6). The dilysate will be loaded onto a SEPHADEX G50 sizing column and eluted at a linear flow rate of 2.5–3 ml×h$^{-1}$×cm$^{-2}$ using elution buffer (100 mM NaCl, 50 mM Tris, 0.4 mM PMSF, 0.02% NaN$_3$). Fractions containing RNase will be identified by catalytic activity against a synthetic RNA (UpA). These fractions will be pooled and concentrated 4-fold using an AMICON ultrafilter device with a YM5 filter ($M_r$>5000 cut-off). This solution will be dialyzed into a new buffer (100 mM NH$_4$OAC, 0.02% NaN$_3$, pH 6.1) and then applied to a column of affinity resin (4 ml, pUp SEPHAROSE, PHARMACIA) by gravity. The eluate under these conditions should be essentially free of RNase activity. The column will be washed with 10–20 volume of buffer, and the RNase will be eluted using a new buffer (200 mM NH$_4$OA$_c$, 300 mM cytidylic acid, pH 6.1). Small fractions (1.5 ml) will be collected. Fractions containing RNase activity will be pooled and dialyzed vs two changes of buffer (100 mM NH$_4$OAc pH 6.1) to remove the cytidylic acid. The solution will be placed in a sterile tube and stored at 4° C. (McGeehan and Benner, supra).

A vector expressing an RNase gene under the control of the $P_R$ promoter can be produced as described in the section entitled RNase gene under control of an inducible promoter.

Induction

Induction can be carried out according to the following method of Okorokov et al., supra). A 6-h culture of the *E. coli* strain carrying the expression vector comprising an RNase gene under the control of the $P_R$ promoter, for example pEXFRA, will be grown in LB medium supplemented with ampicillin (125 µg/ml) at 30° C. at 220 rpm. This culture will be used for inoculation of rich medium containing 24 g/liter yeast extract, 12 g/liter tryptone, 12.54 g/liter, 12.54 g/liter K$_2$HPO$_4$, KH$_2$PO$_4$, 4 ml/liter glycerol, and 125 mg/liter ampicillin and adjusted to pH 7.1.

After growth at 28° C. and 220 rpm in rich medium to a density of OD$_{600}$~0.6, the culture will be induced by heat shock. The following heat shock protocols can be used. The temperature of the culture can be shifted to 42° C. by adding one-half volume of prewarmed (85° C.) rich medium. The culture will then be agitated at 42° C., 120 rpm, for 30 min. The temperature will then be reduced to 37° C. and shaking (220 rpm) will be continued for a further 10 to 12 h.

Alternatively, the temperature of the culture can be shifted to 37° C. by inoculating directly into prewarmed (37° C.) rich medium. The culture will then be grown for an additional 16–18 h at 37° C. and 220 rpm.

2. Inducer Controlled Promoters

The lac operator/promoter in conjunction with the lac repressor can be used to regulate the expression of the RNase gene.

A vector expressing an RNase gene under the control of the lac operator/promoter can be produced as described in the section entitled RNase gene under control of an inducible promoter.

Induction

Fermentation will be carried out in a medium wherein the lac operator is repressed for example LB medium without lactose or isopropyl-β-D-thiogalactoside (IPTG).

Expression will be induced by the addition of IPTG to a final concentration of 0.5 mM or lactose (Neubauer and Hofmann, FEMS Micro. Reviews:14, 99–102, 1994, Quass et al., supra, and Donovan et al., J. Industrial Microbiology, 16: 145–154, 1996). Induction with IPTG can be carried out as described in example 3 below, and according to the method of Quass et al., supra.

To induce transcription of an RNase gene under the control of the lac promoter, IPTG will be added to a final concentration of 0.1 to 0.5 mM to a liquid culture grown to an absorbance of 0.5 at 600 nm. Cells will be allowed to grow overnight and will be harvested by centrifugation (8500×g, 15 min, 4° C.). RNase will be released from the cells by osmotic shock following the modified protocol of Koshland and Botstein. The pellet of a 1 liter culture will be resuspended in 40 ml ice-cold Tris/HCl/EDTA buffer, (50 mM Tris/HCl, pH 7.5, 10 mM EDTA) containing 15% sucrose and kept on ice for 30 min. After centrifugation the cells will be resuspended in ice cold Tris/HCl/EDTA buffer, incubated for another 30 min on ice and centrifuged again. The supernatents from the two washing steps will be combined, the pH adjusted to 2.5 with 15% HCl at 4° C. and the precipitated proteins separated by centrifugation (12000×g, 25 min, 4° C.). The pH of the supernatant will be adjusted to 7.5 with 10 M NaOH, diluted to 200 ml with Tris/HCl EDTA buffer and applied to a DEAE-SEPHAROSE CL-6B column (12 ml column volume) equilibrated with Tris/HCl/EDTA buffer. Recovery will be achieved by gradient elution (100–700 mM NaCl in Tris/HCl/EDTA buffer). Fractions containing RNase activity will be combined and passed through a BIO-GEL P-30 column (1.5×50 cm) using 50 mM ammonium acetate as running buffer (Quass et al., supra).

The strength of the lac promoter could be manipulated to increase expression by cloning the trp promoter upstream of the lac promoter to create the tac promoter.

The affinity of the lac repressor for its operator can be manipulated to increase or reduce binding and, subsequently, expression of the gene under the control of the lac promoter (Müller, et al., J. Mol. Biol., 257: 21–29, 1996).

3. Starvation Inducible Promoters

To control the amount of RNase being produced in a host cell, the RNase gene could be placed under the control of the trp operator in conjunction with the trp repressor.

A vector expressing an RNase gene under the control of the trp operator in conjunction with the trp repressor can be produced as described in the section entitled RNase gene under control of an inducible promoter.

Induction

During growth in the presence of tryptophan, expression of the controlled gene is repressed (Schein & Noteborn, Biotechnology, 6: 291–294, 1988), and upon tryptophan starvation expression of the gene is induced. The trp promoter can also be induced by the introduction of IAA (3-indoleacrylic acid), according to the method of Fujimura et al., supra.

E. coli harboring a plasmid comprising an RNase gene under the control of a trp promoter, for example, pTPW1, will be grown at 37° C. in 4 liters of M9-casamino acid medium containing ampicillin (20 μg/ml). After incubation for 1.5 h (optical density of culture at 660 nm, 0.05–0.1), 3-indoleacrylic acid (IAA, 40 μg/ml) will be added to the medium to induce the expression of the fusion gene. Cells will be allowed to grow further for 8 h, harvested by centrifugation (3500×g, 10 min, 4° C.), and washed in isotonic saline (Fujimura et al., supra).

The following purification steps can be used to purify an RNase protein that has been secreted to the periplasmic space. Proteins in the periplasmic space will be released by osmotic-shock treatment by a modified version of the protocol of Cornelis et al. The saline washed cells will be suspended in 1 liter of 25% sucrose containing 1 mM EDTA and 30 mM Tris-HCl (pH 8.0) and the suspension will be shaken at 37° C. for 30 min. The cells will then be sedimented by centrifugation (14000×g, 1 h, 20° C.), resuspended in 1 liter of ice cold 20 mM Tris-HCl (pH 7.5), and shaken at 0° C. for 30 min. The suspension will be centrifuged (10000×g, 15 min, 4° C.) and the resultant supernatant will be used as the periplasmic fraction. The cytoplasmic fraction will be prepared from sedimented cells by disruption with lysosome in the presence of SDS. RNase will be purified from the periplasmic fraction by two steps of column chromatography: first, anion-exchange chromatography on a Q-SEPHAROSE column equilibrated with 0.15 M NaCl in 20 mM Tris-HCl (pH 7.5) and eluted with a linear NaCl gradient (0.15–0.45 M) in 20 mM Tris-HCl (pH 7.5); then gel chromatography on a SEPHADEX G-50 column from which the enzyme was eluted with 20 mM ammonium bicarbonate. The enzyme at each purification step will be analyzed by SDS-PAGE (Fujimura et al., supra).

4. Bacteriophage Promoters

The T7 RNA polymerase/promoter system includes a promoter that is stronger than the promoter systems described above.

A vector expressing an RNase gene under the control of the T7 RNA polymerase/promoter system can be produced as described in the section entitled RNase gene under control of an inducible promoter.

An RNase gene will be cloned downstream of the T7 promoter (φ10). Expression of T7 RNA polymerase will be controlled by an inducible promoter such as the lacUV5 promoter as is found in E. coli BL21 (Neubauer and Hofmann, supra) or $\lambda P_L$ promoter with the cI857 temperature sensitive repressor (Tabor and Richardson, 82: 1074–1078, 1985).

Expression of the RNase gene will depend upon the expression of the bacteriophage RNA polymerase. In the event that expression of the RNase from the T7 promoter is leaky under uninduced conditions, then a transcriptional terminator for the E. coli RNA polymerase could be inserted into the desired promoter for the T7 RNA polymerase such that expression of the polymerase is dependent upon transcriptional read through (Tabor and Richardson, supra).

Expression of an RNase gene under the control of the T7 promoter can be obtained by the following method of Okorokov et al., supra.

A 6-h culture of the E. coli strain carrying an expression vector comprising an RNase gene under the control of the T7 promoter, for example pETFRA, will be grown in LB medium supplemented with ampicillin (125 μg/ml) at 30° C. at 220 rpm. This culture will be used for inoculation of rich medium containing 24 g/liter yeast extract, 12 g/liter tryptone, 12.54 g/liter, 12.54 g/liter $K_2HPO_4$, $KH_2PO_4$, 4 ml/liter glycerol, and 125 mg/liter ampicillin and adjusted to pH 7.1. After growth at 28° C. and 220 rpm in rich medium to a density of $OD_{600}$~0.6, expression will be induced by adding IPTG to a final concentration of 1 mM with a further incubation for 10 h (Okorokov et al, supra).

5. Inhibitor Induction

The Bacillus RNase, BaRNase, is inactive in the presence of its specific intracellular inhibitor Barstar (Hartley, supra). The presence of the barstar gene in the host cell, which expresses baRNase, suppresses the lethal effect of baRNase activity when both genes are equally expressed. The presence of the barstar gene under the control of a repressible promoter could be used to express baRNase activity at the termination of fermentation.

When the gene for wild-type baRNase, which is lethal alone, is assembled on the same plasmid as the barstar gene on a pUC19-pC194 shuttle vector, baRNase is correctly processed and secreted by Bacillus subtilis but remains cell-bound in E. coli. With barstar and the phoA promoter-signal sequence construct, which has an E. coli signal peptidase site at the N terminus of mature baRNase, following induction by low phosphate, authentic baRNase is secreted by *E. coli* at a level of 20 mg/l. A variable amount of this baRNase, generally about half, will appear in the culture medium, the rest remaining in the periplasmic space. On the addition of acetic acid to 5%, however, all of the baRNase will be released to the medium, from which it may be directly absorbed onto phosphocellulose. More than 90% of the protein eluting from the phosphocellulose in high salt is baRNase. Essentially pure baRNase may then be obtained by salt gradient chromatography on a strong anion exchanger such as SP-TRISACRYL (PHARMACIA) (Hartley, supra).

2. Inducible RNase Expression in the Periplasmic Space or the Cellular Cytoplasm RNase Gene Secreted to Periplasm or Cellular Supernatant To prevent both toxic effects of overproduced RNase on the host cell, and proteolysis of the exogenous RNase by host cell proteases, the RNase gene is modified to encode a protein that is not secreted into the cytoplasm of the host cell. RNases may be produced as fusion proteins with signal peptides that direct secretion of the enzyme to either the periplasmic space or the culture supernatant. The signal peptides that have been used successfully to direct RNase out of the cytoplasm include the endogenous RNase secretion signal (Schein et al., supra, Tarragona-Fiol et al., supra, Russo et al., supra), the *E. coli* alkaline phosphatase signal peptide (phoA) (Fujimura et al., supra, Okorokov et al., supra), the pelB sequence (Ribo et al., supra, DelCardayre et al., supra), and the signal peptide of the OmpA protein of the *E. coli* outer membrane (Quaas et al., supra).

RNase genes may also be expressed as fusion proteins. For example, an RNase A-gene 10 fusion protein is expressed as an inclusion body (Laity et al., supra, Nambier et al., Eur. J. Biochem. 163: 67–71, 1987).

The presence of the gene coding for the Bacteroicin Release Protein (BRP) in a host cell allows for secretion of the overexpressed RNase into the culture supernatant rather than into the periplasm. When the BRP gene is moderately induced, lysis of the host cell is avoided, allowing for large-scale protein production in continuous culture (van der Wal et al., FEMS Microbiol. Rev. 17: 381–399, 1995). This system may be used for secretion of RNase.

By directing the export of the RNase enzyme to a location outside of the host cytoplasm, problems of RNase toxicity and RNase degradation by proteolysis are minimized.

Induction of RNase expression will be regulated according to the parameters defined in the section entitled inducible RNase expression in the cytoplasm. However, RNase will be secreted into the periplasmic space and will not contact the intracellular product until cell lysis.

To target newly made RNase A out of the cytoplasm, a leader sequence can be cloned onto the RNase gene such that the protein is secreted into either the culture supernatant or the periplasmic space.

1. Endogenous RNase Secretion Signal

The *E. coli* RNase I gene has an endogenous leader sequence which directs the gene product to the periplasm, and, when overexpressed on a high copy number plasmid does not affect cell growth (Meador and Kennell, Gene, 95:1–7, 1990).

The endogenous RNase leader sequence can be cloned onto an RNase gene as described in the section entitled RNase gene secreted to periplasm or cellular supernatant.

A number of signal peptides have been used successfully to direct the secretion of an RNase protein to the periplasmic space or the cellular supernatant. These include an endogenous RNase secretion signal, the *E. coli* alkaline phosphatase signal peptide (phoA) and the pelB sequence (Fujimura et al., supra, Schein et al., supra, DelCardayre et al., supra, Okorokov et al., supra, Tarragona-Fiol et al., supra).

2. Pho A

The introduction of a phoA leader sequence onto the baRNase gene which is under the control of a tac promoter has resulted in yields of up to 1 g/l BaRNase (Hartley, supra). This sequence allows for efficient processing and secretion of RNase into the culture supernatant and periplasmic space of the *E. coli* host.

The Pho A sequence can be cloned onto an RNase gene according to the method of Fujimura et al., supra).

A vector containing an RNase gene under the control of a trp promoter is constructed according to the methods of Fujimura et al., supra as described. The trp promoter-containing vector, the RNase gene, and the synthetic gene for the APase signal peptide will be mixed and incubated with T4 DNA ligase, and the desired plasmid, will be obtained from *E. coli* HB101 transformants by standard procedures (Fujimura et al., supra). Fujimura et al. have used this method to construct pTPW1, a vector comprising the RNase T1 gene under the control of the trp promoter. This method can be modified such that the synthetic gene for the APase signal peptide is be cloned onto other RNase genes (including those described) under the control of either a constitutive promoter or one of the inducible promoters described above.

3. Pel B

The Pel B sequence has been used to direct the secretion of RNase to the periplasm in a form that is active following a solubilization step (Ribo et al., supra, delCardayre et al., supra).

The Pel B sequence can be cloned onto an RNase gene by the following method described in delCardayre et al. Plasmid pBXR (where BXR refers to bacterial expression of RNase A) will be constructed as follows. A fragment carrying the cDNA for RNase A that can be inserted between the MscI and SalI sites of pET22B(+) will be generated by PCR. The amplified fragment will be band-purified, treated with T4 DNA polymerase to remove any overhanging bases left by taq polymerase, and digested with SalI. The resulting fragment will have the RNase A cDNA flanked on it 5' end by two CG base pairs (which form a blunt end) and on its 3' end by a SalI sticky-end. This fragment will then be ligated to the band-purified MscI-SalI fragment of the *E. coli* expression plasmid pET22B(+) by T4 DNA ligase. A PstI site in the Amp gene will then be removed by site-directed mutagenesis using oligonucleotide JHH16, malting the PstI site in the RNase A cDNA the only such site in the plasmid. The integrity of this construction will be assessed by restriction and sequence analysis.

Plasmids comprising the pel B sequence cloned onto other RNase genes can also be constructed. A fragment containing the RNase gene and the appropriate restriction enzymes (e.g. sites compatible with linearized pET22B(+) can be ligated as described.

4. Bacteroicin Release Protein

The presence of the gene coding for the Bacteroicin Release Protein (BRP) in the host cell allows for secretion of the over expressed RNase into the culture supernatant rather than into the periplasm. When the BRP gene is moderately induced, lysis of the host cell is avoided, allowing for large-scale protein production in continuous culture (van der Wal et al., FEMS Microbiol. Reviews 17,1995, 381–399).

Cells expressing both an RNase protein and BRP can be made by co-transformation of a plasmid containing the RNase gene with a compatible plasmid containing the BRP gene. Alternatively both genes can be encoded for on the same plasmid.

Expression of the BRP gene can be induced by the addition of MitomycinC (plasmid pSW1 MoBiTec GmbH) or IPTG (plasmid pJL3, MoBiTec GmbH) (See Protocols MoBiTec GmbH, Wagenstief, 5: D-37077 or Van der Wal et al. supra).

The secreted RNase can be purified from the supernatant as described by Tarragona-Fiol et al., (supra) for RNase A, or using THIOBOND resin if the RNase is tagged as a thioredoxin fusion (INVITROGEN) or using PROBOND metal-Binding resin if the RNase is His tagged (INVITROGEN).

The purified RNase can then be added to the cell lysate/supernatant (depending upon location of the desired product e.g. intracellular plasmid/protein or extracellular protein) and incubated until RNA digestion is complete. Plasmid/protein is then purified as described in the section entitled Production of Recombinant DNA or Protein (Horn et al., supra).

5. Fusion Proteins

The RNase gene can also be fused with a gene that allows the RNase protein to be expressed in a soluble form or as inclusion body. For example the RNase gene could be fused with the Thioredoxin gene (R&D SYSTEMS, LaVallie et al, BIO/Technology 11, 1993, 187–193) and, following tryptophan induction, could be selectively released upon freeze/thaw of the bacterial pellet. If the Thioredoxin-RNase fusion protein is active, there is no need to release the thioredoxin by protease cleavage.

The RNase gene of choice can be cloned in frame with the thioredoxin gene in the polylinker of pTRXFUS (INVITROGEN) (LaVallie et al, supra). This vector is then used to transform the production host E. coli G1724. E. coli cells will be cultured to an OD550 of 0.5 and tryptophan added to a final concentration of 0.1 mg/ml, to induce fusion protein synthesis.

If the above production host is also the host for heterologous gene expression or for the production of plasmid then the cells will be incubated until such time as the RNA has been sufficiently been digested. Protein or plasmid purification can then proceed as described.

If the above production host is not the host used for heterologous gene expression or for the production of a heterologous plasmid then the RNase fusion protein can be released by cell lysis (French press) or osmotic shock as described by LaVallie et al. supra, or by freeze thaw as described by Johnson & Hecht, M. H. Bio/Technology 12:1357–1359, 1994. The released protein can then be purified using a THIOBOND resin as described by INVITROGEN or as described by Tarragona-Fiol et al. Supra.

The purified RNase can then be added to the cell lysate of the host cell producing the heterologous gene or plasmid as described (see Birnboim and Doly, supra and Ausubel, Current Protocols, supra).

RNase Gene Under Control of a Constitutive Promoter

In some methods and host cells according to the invention, it will be preferred to constitutively express the RNase gene. Thus, the RNase gene will be placed under the transcriptional control of a constitutive promoter that is operable in the selected host cell. Constitutive promoters are well-known in the art for many different types of bacteria. For example, in E. coli, such promoter include the glucokinase promoter of the 6-phosphogluconate dehydrogenase promoter (Neidhardt, in Salmonella typhimurium and Escherichia coli Cellular and Molecular Biology ASM, Fraenkel, D., Chapter 12, 0.142, 1987).

Constitutive Periplasmic Expression of RNase

An RNase gene can be engineered to produce protein that is constitutively expressed and localised in the periplasm as described in the section entitled RNase gene under control of a constitutive promoter.

To achieve constitutive RNase expression in the periplasm, an induction period is not required. RNase will accumulate in the periplasm as cells grow (Tarragona-Fiol et al., supra).

RNase Digestion in Host Cells Secreting RNase into the Culture Supernatant

If both the cellular component of interest and the RNase are secreted into the supernatant, whether by the same cell or different cells, cell lysis should be avoided since the product of interest will be contaminated by components released from bursting/dying cells. For example, bovine RNase A is very stable and is still active in fermentation broth at pH 6.8–7.4.

The cellular components can be collected directly from the culture supernatant without releasing other cellular derived contaminants by lysing cells. Cells will be removed from the supernatant by centrifugation for 25 min at 10,000 g. The cell-free supernatant, which contains both the cellular component and the RNase, will be incubated until substantially all of the RNA has been degraded.

The optimal incubation period is the time required to degrade substantially all of the RNA from a cellular component that is either a protein, DNA or CHO (as defined herein). The optimal incubation period required to degrade substantially all of the RNA from a cellular component will be determined by the following steps. At appropriate time points (5 minute intervals, up to 1 hour or more if the undegraded RNA is still present, as determined by methods described below) aliquots will be removed and assayed for the presence of RNA, by the methods described below.

Following removal of RNA the cellular component can be purified as described below.

Alternatively, it is possible to directly capture the product by applying the culture medium to an expanded bed chromatography column. According to this protocol, cells and RNase will pass directly through the column while the product will bind to the chromatography medium according to the method of Hansson et al., Bio/Technology, 12: 285–288, 1994 described below.

Equipment for expanded bed adsorption. A STREAMLINE 50 (inner diameter of 50 mm) borosilicate glass column (PHARMACIA BIOTECH, Uppsala, Sweden), equipped with a purpose-designed liquid distributor at the bottom of the column, can be used together with the STREAMLINE DEAE adsorbent (PHARMACIA BIOTECH, Uppsala, Sweden), for the ion exchange adsorption in an expanded bed procedure. The absorbent matrix consists of spherical macroporous, cross-linked agarose particles, containing crystalline quartz to increase the bead density (mean particle density=1.2 g/ml). The ionic capacity for the diethylaminoethyl (DEAE) absorbent is 0.13–0.21 mmol/ml. The particle size distribution ranges from approximately 100 to 300 $\mu$m with a mean particle size of 200 $\mu$m. The adsorbent is autoclavable, has an operational pH stability between 3 to 9 and resists 1M NaOH. The bed height in sedimented configuration will be 10 cm. The linear flow rate recommended to give a suitable expansion of the bed is 200–400 cm/h. The capacity of the adsorbent to bind the target protein should be investigated in packed bed column experiments prior to setting up the process.

Expanded bed adsorption. At the end of the fermentation the pH will be allowed to drop to 5.5 by removal of the base addition for pH control $NH_3$-regulation or NaOH-regulation. In addition, the glycerol feed will be terminated and the temperature will be raised to 60° C. for 20 minutes to increase the leakage of periplasmic proteins to the culture medium. The culture, thereafter, will be cooled to room temperature. Prior to loading, the bed will be pre-expanded two to three times with loading buffer (50 mM NaCl) at a linear flow rate of 200 cm/h. The crude fermentor broth will then be applied, from bottom to top, to the expanded bed as a 1:1 mixture with loading buffer, at the same total flow rate (200 cm/h), using a two pump arrangement allowing on line mixing. When the entire fermentor content has been loaded, the expanded bed will be kept in an expanded state by increasing the loading buffer flow rate to 200 cm/h. Approximately ¼ volume of loading buffer and thereafter ½ volume of washing buffer (100 mM NaCl) will be allowed to pass through the expanded bed to wash out remaining cells and loosely adsorbed proteins. The anionic adsorbent will then be sedimented by reversing the flow and lowering the adapter to the top of the packed bed, which will have been washed with washing buffer. The packed bed will then be eluted from top to bottom using 0.5 M NaCl (flow rate 100 cm/h) and 50 ml fractions will be collected.

Analysis by viable count and OD measurements of the cell removal efficiency of the expanded bed. Samples from the bed outlet will be collected during the washing procedure. For the viable count analysis the samples will be diluted to two separate dilutions (differing a 100-fold). A volume of 100 $\mu$l of each sample will be plated on Trypticase Blood Agar Baseplates supplemented with ampicillin (0.1 g/l). The plates will be incubated at 37° C. overnight and the number of colonies will be counted. For OD measurements the samples will be diluted to give A600nm values of 0.2–0.8. For lower cell contents than A600nm=0.01, an only viable count will be performed. A cell content up to $10^6$ cfu/ml is below the detection level of OD measurements, indicating that a visually clear culture medium could contain 100,000 cells per ml (Hansson et al., supra).

Lysis and RNase Digestion in Cells Expressing RNase in the Periplasm or Cytoplasm If the RNase accumulates extracellularly in the culture supernatant and the cellular component accumulates within the cell (cytoplasm or periplasm), cell lysis is required to allow the product and contaminating RNA to come into contact with extracellular RNase.

Cells expressing RNase in the periplasm or cytoplasm can be lysed according to the methods described in Scopes, supra or LaVallie et al., supra.

Determination of Residual RNA

The invention contemplates methods for producing a cellular component that is substantially RNA-free. In order to determine whether a cellular component prepared according to the inventive methods is substantially RNA-free, the following protocols may be used.

RNA in DNA Sample

1. Agarose Gel Electrophoresis Based Methods for RNA Detection

Samples Preparation

Each DNA sample is initially diluted to a concentration of approximately 0.2 $\mu$g/$\mu$l. Samples are then mixed in a 1:1 ratio with 2×loading buffer to a final concentration of approximately 0.1 $\mu$g/$\mu$l. 10×Stock Loading Buffer is 20% w/v glycerol, 1% w/v SDS, 0.25% w/v bromophenol blue in 0.1 M $Na_2EDTA$ (pH8.0). RNA control standards are prepared by adding 1 $\mu$l of an approximately 1 mg/ml RNA stock solution for every 50 $\mu$l of sample to replicate samples of DNA. 10 $\mu$l of each sample are analyzed on a 1% agarose gel along with an aliquot of a 1 kb ladder marker (LIFE TECHNOLOGIES Ltd). Agarose gels will be run in 1×TAE buffer (40 mM Tris acetate, 2 mM EDTA) made from a 50×Stock solution.

Standards for Electrophoresis

Electrophoresis standards can be prepared by the following method. Prepare a solution of RNA Type III (from Baker's Yeast (SIGMA)) at a concentration of 1 mg/ml in deionized water. This solution will then be diluted 1:5 to a concentration of 0.2 $\mu$g/$\mu$l, and then 1:1 with 2×loading buffer (see recipe above) to a concentration of ~0.1 $\mu$g/$\mu$l. Load 10 $\mu$l of this solution onto the gel for a 1 $\mu$g RNA standard. Additional load 10 $\mu$l of serial dilutions of this solution prepared according to the following method.

Add 100 $\mu$l of the 0.1 $\mu$g/$\mu$l stock solution (in loading buffer) described above to tube 1. Remove 50 $\mu$l from tube 1 and add this sample to 50 $\mu$l 1×loading buffer (tube 2). Mix well by pipetting. Remove 50 $\mu$l from tube 2 and add this sample to 50 $\mu$l of 1×loading buffer (tube 3). Continue diluting the standard solution until 12 tubes have been prepared. Load 10 $\mu$l according of each standard solution onto an agarose gel.

Electrophoresis Conditions

Voltage: 100 V (Controlled)

Current: 400 mA (Maximum)

Power: 100 W (Maximum)

Time: 30 minutes

Analysis of Results

The gel is stained to visualise nucleic acid and photographed on a UV transilluminator at 254 nm.

To detect RNA, following agarose electrophoresis, the gel is stained with either ethidium bromide or sybr Green II. RNA is visualized under UV illumination. The detection limit for ethidium bromide and sybr green II staining is approximately 3.2% w/w (RNA/total nucleic acid) and 1.6% w/w (RNA/total nucleic acid) respectively.

Ethidium Bromide

If the gel is to be visualized by ethidium bromide staining, add Ethidium Bromide to the agarose gel at a final concentration of 0.5 $\mu$g/ml and to the running buffer at a concentration of 0.5 $\mu$g/ml. Ethidium Bromide is added from a 1 mg/ml stock solution (1 tablet of ethidium bromide per 100 mls sterile water—SIGMA lot 35H0868) stored at 4° C.

The limits of detectability can be determined by observing which standard dilution does not permit the visualization of RNA. The preceding standard load is then expressed as a percentage of the stock standard loading (1 $\mu$g.) If no RNA is observed in the sample tracks then quote the result as "less than X% w/w," where X is the calculated sensitivity. Should a band be observed, compare its intensity with that of the standards and estimate the amount as an amount between that of the two standards between which the sample result lies. Quote the result on a less than/more than basis. A substantially RNA-free sample, according to this method, is less than 3.2% w/v, i.e. no RNA is detected.

Sybr Green II

To prepare a SYBR Green II solution, dilute the stock solution of SYBR Green II dye (from MOLECULAR PROBES) by 1:10,000 in TBE buffer (89 mM Tris base, 89 mM Boric acid, 1 mM EDTA, pH 8.0). This solution can be stored in a polypropylene bottle, wrapped in aluminium foil at 4° C.

Following electrophoresis, stain the gel with SYBR Green II dye, prepared as described above, for 30 minutes at 4° C. in the dark.

Determine the sensitivity of the gel by observing which standard dilution equates to no observable RNA. The preceding standard load is then expressed as a percentage of the stock standard loading (1 µg.) If no RNA is observed in the sample tracks then quote the result as "less than X% w/w," where X is the calculated sensitivity. Should a band be observed compare its intensity with that of the standards and estimate between which two standards the sample result lies. Quote the result on a less than/more than basis. A substantially RNA-free sample, according to this method, is less than 3.2% w/v, and preferably less than 1.6% w/w (i.e. no RNA is detected).

Materials and Methods for Staining with Ethidium Bromide or Sybr Green

Equipment: PHARMACIA BIOTECH Electricity Power Supply (or similar) an ANACHEM Electrophoresis Units (16 sample wells/two rows minimum) and a UV Transilluminator with 254 nm illumination.

2. Northern Blot Analysis

Northern blot analysis of an experimental sample and standards for electrophoresis (as described in the section entitled agarose gel electrophoresis based methods for RNA detection) can be performed according to the method described in Current Protocols, supra. To detect residual RNA, add Ethidium Bromide to the formaldehyde/agarose gel at a final concentration of 0.5 µg/ml and to the MOPS running buffer at a concentration of 0.5 µg/ml. Following agarose/formaldehyde electrophoresis the gel will be rinsed in distilled $H_2O$ for 30 min. RNA will then be visualized under UV illumination.

The limits of detectability can be determined by observing which standard dilution does not permit the visualization of RNA. The preceding standard load is then expressed as a percentage of the stock standard loading (1 µg.) If no RNA is observed in the sample tracks then quote the result as "less than X% w/w," where X is the calculated sensitivity. Should a band be observed, compare its intensity with that of the standards and estimate the amount as an amount between that of the two standards between which the sample result lies. Quote the result on a less than/more than basis. A substantially RNA-free sample, according to this method, is less than 3.2% w/v, i.e. no RNA is detected.

2. RNA Detection by HPLC Assay.

According to this method, residual RNA is hydrolyzed into its constituent ribonucleotides under mildly basic conditions. The ribonucleotides are treated with an alkaline phophatase enzyme to produce ribonucleosides, which may be resolved under reverse phase high performance liquid chromatography (RPHPLC). To ensure that the DNA present in the sample does not interfere with the assay, a spin filtration step is done to remove the DNA from the sample prior to analysis.

The RPHPLC conditions have been optimized for sensitivity such that this method has a limit of detection in the picomolar region; or approximately 0.1% when expressed as a percentage of the total concentration of DNA or protein.

RPHPLC Conditions;

Instrument: HEWLETT PACKARD 1100 HPLC system. Or equivalent system capable of gradient elution and detection in the UV region.

Column: SUPELCOSIL LC-18S 25 cm*2.1 mm 5 µm. (Or similar)

Mobile Phase: A=10 mM $NaH_2PO_4$ pH 6.0 (97.5%); Methanol (2.5%)

B=Methanol

Gradient: 0 to 20% B over 30 minutes

Run time: 45 minutes in total.

Flow rate: 0.21 ml/min

Loading: 5 µl

Detection: UV at 260 nm

RPHPLC Standard preparation.

To prepare standards, transfer approximately 15 mgs of each ribonucleoside to a 50 ml volumetric flask. Dissolve the ribonucleosides and bring them to volume in mobile phase A. Combine 200 µl of each ribonucleoside into a 1.5 ml EPPENDORF tube and perform serial two-fold dilutions, seven times. The resulting solution can be chromatographed directly using the above conditions. The Guanosine standard may require warming and sonication to aid dissolution. Calculate the standard loading for each ribonucleoside as follows (the RMM of the ribonucleoside should be used and the result should be quoted in picomoles);

$$(Wt(g) \times 0.2 \times 1000 \times 5 \times 1)/(RMM \times 0.8 \times 50 \times 1000000 \times 2^7)$$

RPHPLC Sample Preparation:

Prepare samples by adding 5 µl of a 3M solution of potassium hydroxide to 50 µl of sample plasmid DNA. For examples, the samples can be plasmid DNA at 2 to 3 mg/ml in Water For Injection, WFI. The solution is briefly vortex mixed and then incubated at 37° C. for a minimum of 16 hours. Equal volumes of 3M acetic acid and a 1M tris buffer (pH 8) are then added; followed by the addition of 10 µl of a 100 U/ml suspension of bacterial alkaline phosphatase (BAP). The resulting solution is then briefly vortex mixed and incubated at 37° C. for an additional two hours. Immediately prior to analysis the samples are placed into spin filters with molecular weight cut off membranes operating at 10,000 daltons (or as appropriate) and centrifuged at 13,000 for 10 minutes. The filtrate is chromatographed without further treatment according to the conditions described above.

Results:

To interpret the results, integrate the peaks corresponding to cytidine, uridine, guanosine and adenosine (the peaks will elute in this order) in the sample and in the standard chromatograms. The amount of each ribonucleotide in the sample is then calculated as follows (the RMM used here is that of the monophosphate ribonucleotide, if the standard load is quoted in picomoles then the result will be given in nanograms). The detection limit for this method is about 0.1% w/w. A substantially RNA-free sample according to this detection method is less than 1.6% and preferably less than 0.1 to 0.5% w/w.

$$(A \times C \times D \times 75)/(B \times 5)$$

Where;

A=Loading of standard ribonucleoside in picomoles.

B=Area under the peak due to the standard ribonucleoside.

C=Area under the peak due to the sample ribonucleoside.

D=RMM of the ribonucleotide monophosphate.

Sum the results obtained for each ribonucleotide to give a total RNA content. The final result is quoted as a mass and may be used to quote the result as a percentage of the DNA or protein content (% w/w), or of the solution volume (% w/v).

2. RNA in Protein Samples

Residual RNA can be detected in protein samples by either the agarose gel staining methods (as described) or the HPLC assay as described. The detection limit for this method is about 0.1% w/w. A substantially RNA-free sample according to this detection method is less than 3.2% w/w, preferably less than 1.6% and preferably less than 0.1 to 0.5% w/w.

An acceptable level of RNA contamination of therapeutic plasmid DNA is <1% w/w. An acceptable level of RNA contamination of therapeutic protein is <10 ng/dose.

Determination of Amount of RNase in a Cell Lysate

An advantage of the invention is that significantly less RNase protein is needed to remove substantially all of the RNA molecules in a cell lysate, and thus significantly less RNase protein is present in the lysate.

The amount of RNase protein present in a cell lysate may be determined by the following methods.

RNase I Assays

Three different assays for RNase I can be used to estimate enzyme in cell extracts. Assay A measures acid-soluble ultraviolet-absorbing material released from RNA. Assay B is a more sensitive and more specific modification of assay A. $^{32}$P-labeled RNA is the substrate and acid-soluble radioactive material is measured. Assay C is a sensitive method for assaying RNase I in ribosome preparations. This consists of measuring the release of ultraviolet-absorbing material from ribosomes dialyzed against urea-containing buffer. All three assays reveal latent RNase I, since, in A and B, EDTA leads to activation of the enzyme, and in C, urea causes activation. Polynucleotide phosphorylase and RNase II are inhibited by EDTA and urea and are relatively inactive on RNA.

(i) Assay A

A 0.1 ml reaction mixture will contain, 10 µmoles potassium phosphate buffer, and 1.0 µmole EDTA, all adjusted to pH 7.0, plus the enzyme fraction. After incubation at 37° C. for 40 min, 0.3 ml of cold 3% $HClO_4$ will be added and the mixture will be cooled in ice for 15 min. After centrifugation for 15 min at 2000 g in the cold, 0.1 ml of the supernatant solution will be diluted into 1.0 ml of distilled water and the $OD_{260}$ determined. All assays will be carried out in duplicate and values will be corrected for any acid-soluble ultraviolet-absorbing material in the enzyme fraction. Activity is expressed as µµmoles of acid-soluble nucleotide/reaction mixture/hr, assuming a molar extinction coefficient of 10,000 for the nucleotides (Gesteland, J. Mol. Biol. 16: 67–84).

(ii) Assay B $^{32}$P-labeled RNA will be added to the reaction mixture in assay A, keeping the total substrate concentration constant. The final specific activity of the RNA will be 2000 to 5000 cts/min/0.1 mg. After incubation, precipitation and centrifugation as in A, 0.2 ml of the supernatant solution will be removed and placed on a 5 cm aluminium planchet and dried for counting. As in assay A, activity is expressed as µµmoles/hr based on the specific activity of RNA in the reaction mixture (Gesteland, supra).

(iii) Assay C

VISKING dialysis tubing (8/22) will be boiled in dilute $Na_3CO_2$ for 20 min, washed thoroughly in distilled water and stored in 0.1 ml mM EDTA. Just before use, the tubing will be washed again with distilled water. All glassware will be sterilized, and disposable plastic gloves will be used in handling the dialysis tubing in order to minimize RNase contamination. 1.0 ml (containing 30 µmoles of nucleotides) of a solution of ribosomes that had been washed 3 times in 0.01 M-magnesium acetate, 0.005 M-tris (pH 7.5) will be dialyzed against 100 ml of 4 M-urea, 0.005 M-tris (pH 7.5), 0.05 M-KCl at 4° C. At various times a sample of the dialysis buffer will be removed and the $OD_{280}$ measured. Results will be expressed as mµmoles of nucleotide released/min/mole of nucleotides in the original ribosomes (Gesteland, supra).

RNase A assays (Suitable for all Non-specific RNases)

Recombinant RNase Activity on RNA Agar Plates.

A solution containing 2% (w/v) agar (Bacto-agar)/100 mM MES pH 6.5 0.3% (w/v) yeast RNA will be autoclaved and poured in Petri dishes. Round holes will be made in the RNA agar using a sterile cork-borer, and recombinant or commercial RNase (0.1–25 µg) will be applied in a volume of 150 µl. The plates will be incubated for 2–4 h at 37° C. To visualize RNase activity, 2 M HCl will be poured over the plate. A clear zone will be produced around the hole were active RNase has been introduced and RNA that had not been hydrolyzed forms a cloudy precipitate (Tarragona-Fiol et al., supra).

The amount of RNase in a cell lysate can also be measured by determining the rate of hydrolysis of cytidylyl-3':5'-adenosine by RNase. The hydrolysis of CpA by RNase can be carried out at room temperature in 1-ml, 1-cm path cuvets (Hellma). The volume of the reaction will be 1 ml. Reactions containing 0.1 mM CpA in 0.1 Trisxacetate pH 6.5 will be initiated by adding a lysate containing RNase. The hydrolysis of CpA will be measured, against a blank containing 0.1 M Trisxacetate pH 6.5 and 0.1 mM CpA, by an increase in $A_{265}$ nm (Tarragona-Fiol et al., supra).

EXAMPLE I

Small Scale Purification of a pUC18-based *E. coli* RNaseI Expression Plasmid from *E. coli* DH5a without RNase A Treatment The RNaseI gene was amplified from *E. coli* strain DH1 by PCR using the primers, 5'-GGTCCTGGGGTGA TTATTTACGGCTGTGGC-3'SEQ ID NO:7 and 5'-GTTTA ACTCACATGATGATACTGACTGTTG-3' SEQ ID NO:8 and cloned into the TA cloning vector pCR3.1 (INVITROGEN Inc.) as described.

Figure 3:
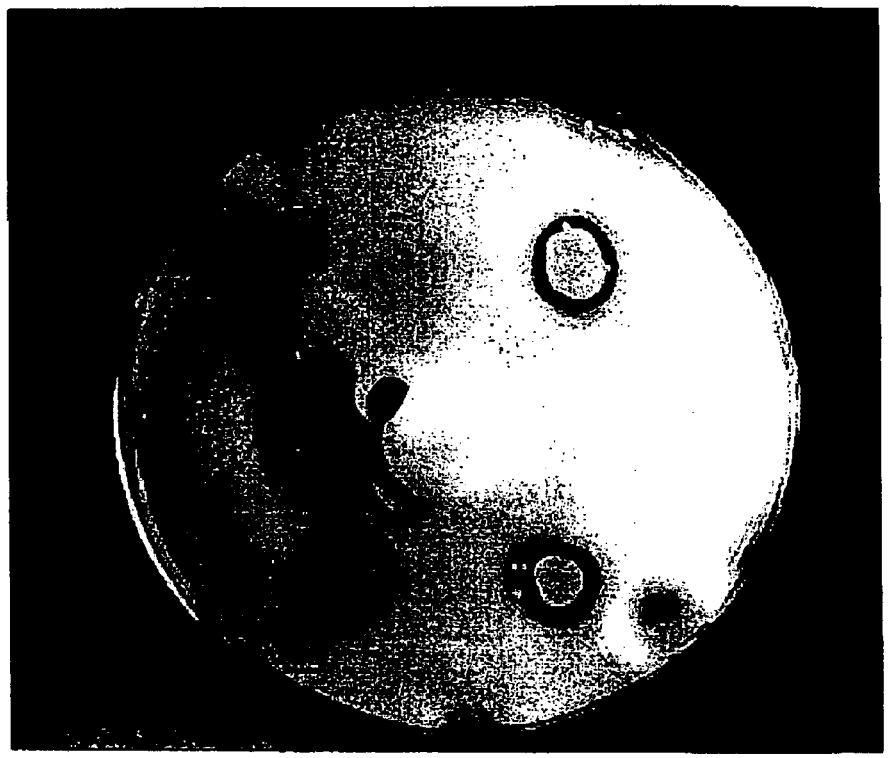
FIG. 3 is an LB agar plate assay demonstrating expression of RNase I from TOP10F cells transformed with pCR3.1RNase I.

RNase I plate assays demonstrated that the resulting vector overexpressed the RNase I gene in *E. coli* TOP10F (FIG. 3) and DH5α (data not shown). RNase plate assays were performed by the following method. LB agar (supplemented with kanamycin at 30 µg/ml) was spotted with 10 µl of overnight cultures of: 1. (Top left) TOP10F clone 1 (pCR3.1), 2. (Top right) TOP10F clone 2 (pCR3.1 RNase I), 3. (Middle left) TOP10F clone 3 (pCR3.1 RNase I), 4. (Middle Right) TOP10F clone 4 (pCR3.1), 5. (bottom left) TOP10F clone 5 (pCR3.1 RNase I) and 6. (Bottom Right) TOP10F clone 6 (pCR3.1 RNase I) and incubated at 37° C. overnight. The following day the plate was overlaid with 6 ml of soft agar containing baker's yeast RNA (0.3% in 11 mM EDTA. After incubation at 37° C. for 4 hours, the plate was developed by the addition of 10 ml of 1M HCl, and photographed.

Figure 4:
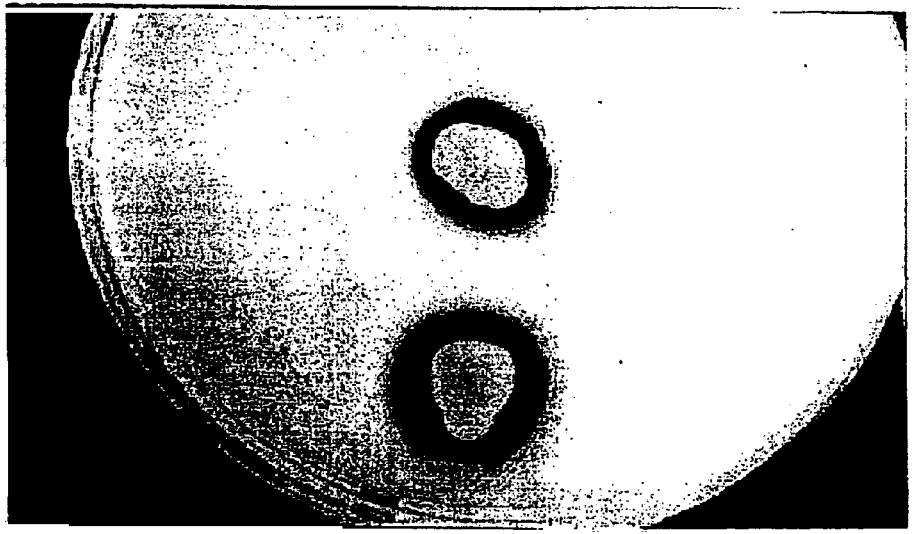
FIG. 4 is an LB agar plate assay demonstrating IPTG inducible expression from DH5α cells transformed with pUC18RNase I.

The RNaseI gene was then cloned into pUC18 downstream of the lacZ promoter such that its expression was increased upon the addition of IPTG to a final concentration of 0.5 mM. Plate assays showed expression from the pUC18 construct was marginally higher than from the pCR3.1 construct in DH5α following induction (FIG. 4). LB agar (supplemented with ampicillin at 50 μg/ml and IPTG 0.5 mM) were spotted with 50 μl of overnight cultures of 1. (Top) DH5α (pCR3.1 RNase I) and 2. (Bottom) DH5α (pUC18 RNase I) cultures and incubated at 37° C. overnight. The following day the plate was overlaid with 6 ml of soft agar containing baker's yeast RNA (0.3%) in EDTA (11 mM). After incubation at 37° C. for 4 hours the plate was developed by the addition of 10 ml of 1M HCl, and photographed.

Figure 5:
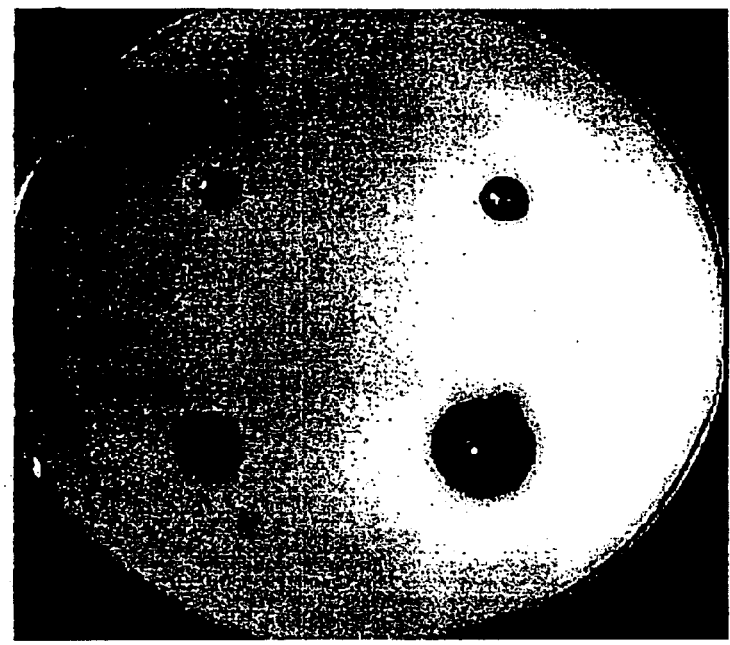
FIG. 5 is an LB agar plate assay demonstrating the sensitivity of purified pUC18 RNase I to alkaline lysis.

When plasmids were isolated by alkaline lysis from strains containing these constructs it was apparent that the overexpressed RNaseI was unable to remove RNA from these samples whereas the addition of exogenous bovine RNaseA could remove RNA from replicate samples. Plate assays suggested that RNaseI was either not synthesised in sufficient quantities or was sensitive to the alkaline lysis procedure (FIG. 5), and in particular to the denaturation step in the presence of SDS and sodium hydroxide.

LB agar (1%) plates containing baker's yeast RNA (0.3%), Tris buffer (10 mM) and EDTA (11 mM) were loaded with the following samples.

1. (Top Left) DH5α (pUC18 RNase I) cells resuspended in TE buffer, lysed by the addition of 0.2M NaOH and 1% SDS and neutralised by 3M potassium acetate. The supernatant from these cells was clarified by centrifugation and 60 μl was loaded into a well in the plate;

2. (Top Right) DH5α (pUC18 RNase I) cells resuspended in TE buffer and lysed by three cycles of freezing and rapid thawing. The supernatant from these cells was clarified by centrifugation and 20 μl was loaded into a well in the plate;

3. (Bottom Left) DH5α (pUC18 RNase I) cells resuspended in TE buffer and lysed sonication. The supernatant from these cells was clarified by centrifugation and 20 μl was loaded into a well in the plate; and 4. (Bottom Right) 2 μg of bovine RNase A in 20 μl of TE buffer loaded into a well in the plate. The plate was incubated at 37° C. for 4 hours and then developed by the addition of 10 ml of 1M HCl before being photographed.

Figure 6:
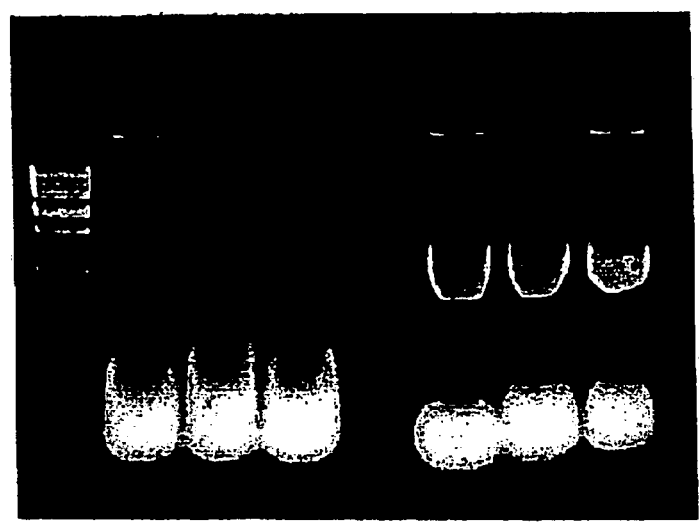
FIG. 6 is an ethidium bromide stained agarose gel demonstrating the affects of lysis conditions on the activity of pUC18 RNase I.

When the protocol for small scale purification of recombinant plasmid DNA from RNaseI expressing strains was modified to include an extended incubation period (Birnboim and Doly, 1979) overexpressed RNaseI removed a portion of the contaminating RNA from the preparation of plasmid DNA (FIG. 6).

Specifically, the alkaline lysis procedure was modified to include a period of incubation following the neutralization step or following release of RNaseI by sonication/freeze thaw and prior to denaturation with sodium hydroxide and SDS. During this incubation period RNA was digested by the expressed RNase.

FIG. 6 is an Ethidium bromide stained 0.8% agarose gel loaded with 5 μl of the following samples prepared as described:

Lane 1. DNA fragment size marker 1 BstEII;

Lane 2. DH5α (pUC18) cells resuspended in TE buffer, lysed by the addition of 0.2M NaOH and 1% SDS, neutralised with 3M potassium acetate and incubated on ice for 2 hours. The supernatant was clarified by centrifugation, ethanol precipitated and resuspended in 20 μl of TE buffer;

Lane 3. DH5α (pUC18) cells resuspended in TE buffer and lysed by 3 cycles of freezing and rapid thawing and incubated on ice for 2 hours. The sample was then treated with 0.2M NaOH and 1% SDS, neutralised by 3M potassium acetate and clarified by centrifugation. DNA was ethanol precipitated and resuspended in 20 μl of TE buffer;

Lane 4. DH5α (pUC18) cells resuspended in TE buffer and lysed by sonication. After incubation on ice for 2 hours, the sample was treated with 0.2M NaOH and 1% SDS, neutralised by 3M potassium acetate and clarified by centrifugation. DNA was ethanol precipitated and resuspended in 20 μl of TE buffer;

Lane 5. Empty;

Lane 6. DH5α (pUC18 RNase I) cells resuspended in TE buffer, lysed by the addition of 0.2M NaOH and 1% SDS and neutralised by 3M potassium acetate and incubated on ice for 2 hours. The supernatant was clarified by centrifugation, ethanol precipitated and resuspended in 2 μl of TE buffer;

Lane 7. DH5α (pUC18 RNase I) cells resuspended in TE buffer, lysed by 3 cycles of freezing and rapid thawing and incubated on ice for 2 hours. The sample was then treated with 0.2M NaOH and 1% SDS, neutralised by 3M potassium acetate and clarified by centrifugation. DNA was ethanol precipitated and resuspended in 20 μl of TE buffer;

Lane 8. DH5α (pUC18 RNase I) cells resuspended in TE buffer and lysed by sonication. After incubation on ice for 2 hours, the sample was treated with 0.2M NaOH and 1% SDS, neutralised by 3M potassium acetate and clarified by centrifugation. DNA was ethanol precipitated and resuspended in 20 μl of TE buffer.

EXAMPLE II

Use of E. coli DH1RNase A (Constitutively Expressing RNase A) for Production of Plasmid pUC19tet and Protein An RNase A gene can be cloned under the control of the constitutively active glucokinase promoter and inserted into the chromosome of the E. coli host strain DH1 using pN1 as an intermediate plasmid (as described in the section entitled Integration of an RNase gene into the chromosome). RNase A protein will be directed to the periplasm by its endogenous leader sequence.

Plasmid production in DH1RNase A E. coli cells transformed with the plasmid of interest (for example, pUC19tetΔAmp or pTX0161 described in WO 97/29190), which also expresses a chromosomal RNase A gene under the control of the constitutively expressed glucokinase promoter, grown and lysed by alkaline lysis, as described above in the section entitled Purification of Recombinant DNA or Protein, will be performed according to the method described in WO 97/29190. The lysis protocol will be modified so that it does not include a step in which the sample is incubated with exogenously added RNase A but instead is incubated with its autologously produced recombinant RNase A.

DH1RNase A E. coli cells will be transformed with a plasmid containing the gene for Influenza Nuclear Protein (NP) cloned in frame into the expression vector pTRCHis (INVITROGEN). The cells can be cultured as described above in the section entitled Purification of Recombinant DNA or Protein according to the method of Horn et al., supra. The cells will constitutively synthesize influenza virus nuclear protein (NP). The cells will lysed using a cell homogenizer and incubated for a length of time sufficient to produce a substantially RNA-free recombinant protein, according to the invention. The presence of residual RNA will be detected according to the methods described in the section entitled detection of residual RNA. The NP protein will be purified according to the following method.

Extraction and Purification

Cells will be harvested by centrifugation, resuspended in 1% lysis buffer (50 mM $NaPO_4$, 1M NaCl, 0.5% sarkosyl) and frozen at −80° C. Cells will be thawed on ice in the presence of protease inhibitors (BOEHRINGER MANNHEIM complete EDTA free protease inhibitor cocktail tablets, 1 tablet/50 ml of cell resuspension). DNase I will be added to a final concentration of 5 mg/ml. The cell pellet will be lysed by homogenization at 30 Kpsi using a single pass in a CONSTANT SYSTEMS Ltd homogenizer. Alternative homogenization methods can be found in Scopes, supra. The lysate will be subjected to centrifugation at 10,000 g to remove cell debris. Sarkosyl will be added to a final concentration of 0.5% to aid protein solubility and endotoxin removal. Following the addition of 60 ml of 50% Ni-NTA agarose (QIAGEN Inc.), the lysate will be incubated for 1 hour at 4° C. to allow batch binding of the protein to occur.

The bulk of the lysate will be removed from the resin by centrifugation at 200 g. The resin will be resuspended in the remaining lysate and used to pour a PHARMACIA XK 26 column. The column will be washed with 400 ml Wash Buffer (50 mM $NaPO_4$, 1M NaCl, 0.5% sarkosyl, 20 mM imidazole, 10% glycerol). Contaminants will be eluted with a gradient of 0% to 22% 0.5M imidazole in wash buffer. The recombinant NP (rNP) will be eluted with a step gradient of 100% of 0.5% imidazole in wash buffer using a fraction collector.

The appropriate fraction will be analyzed by SDS-PAGE to verify the presence of rNP. The fractions containing the highest concentration of rNP will be pooled (pool 1). Additionally, the fractions containing the lowest concentration of rNP will be pooled (pool 2).

Pooled rNP will be dialyzed into 25 mM Hepes, 0.5% sarkosyl. The protein concentration will be determined by using a BIORAD protein assay. The presence of residual endotoxin will be determined by KQCL assay (BIOWITTAKER). The presence of residual RNA will be determined according to the methods described in the section entitled Determination of Residual RNA.

EXAMPLE III

Use of *E. coli* DH1RNase A (Inducible and Periplasmic) for the Production of Plasmid pUC18 and Protein An RNase A gene can be cloned under the control of the inducible lac promoter and stably integrated into the chromosome of DH1, using pN1 as an intermediate plasmid, according to the methods described above. RNase A protein will be directed to the periplasm by its endogenous leader sequence.

The *E. coli* cells are then transformed with the plasmid vector to be purified (for example, pUC19tetΔAmp or pTX0161) grown according to the methods described above in the section entitled Purification of Recombinant DNA or Protein, according to the method described in WO 97/29190. RNase A production will be induced by the addition of 0.5 mM IPTG prior to the termination of fermentation. Cells will be lysed by the modified alkaline lysis procedure described in example II and the plasmid purified by the procedure described in WO 97/29190.

*E. coli* cells transformed with a vector comprising the NP gene cloned in frame into the expression vector pTRCHis (INVITROGEN) and can be cultured as described above in the section entitled Purification of Recombinant DNA or Protein according to the method described in WO 97/29190. The cells can be induced to synthesize RNase and NP protein simultaneously by the addition of 0.5 mM IPTG as described above, lysed using a cell homogenizer and incubated for 10 to 60 minutes to remove RNA. The NP protein will be purified according to the methods described above (Example II and Scopes, supra).

EXAMPLE IV

Use of *E. coli* BL21(DE3)RNase A (Inducible and Periplasmic) for the Production of Plasmid and Protein An RNase A gene can be cloned under the control of the inducible T7 promoter and stably integrated into the chromosome of BL21 (DE3), using pN1 as an intermediate plasmid, according to the methods described above. RNase A protein will be directed to the periplasm by its endogenous leader sequence.

*E. coli* cells transformed with the plasmid of interest (for example, pUC19tetΔAmp or pTX0161) and carrying the chromosomal expression cassette BL21 (DE3) RNase A comprising an RNase A gene under the control of the T7 promoter can be grown in shake flasks in LB medium. RNase A production will be induced as described in Example V below or according to the methods described in the section entitled Inducible Promoter Systems. Cells will be lysed by the modified alkaline lysis procedure described in example II and the plasmid purified as described in WO 97/29190.

*E. coli* cells BL21 (DE3) RNase A can be transformed with a vector comprising the NP gene cloned in frame into the expression vector pET (under the control of the T7 promoter). This vector is called pTX030 and is described in Example V below. The vector is cultured as described below. The cells can be induced to synthesize NP as described below, lysed using a cell homogenizer and incubated for 10 to 60 minutes to remove RNA. The NP protein will be purified according to the methods described above (Example II and Scopes, supra).

EXAMPLE V

RNA Free Influenza Virus Nuclear Protein Production in *E. coli* BL21(DE3) RNase A

*E. coli* BL2(DE3) RNase A can be produced according to the methods described for the production of DH1RNase A, using the target strain BL21(DE3) to generate BL21(DE3) RNase A in the P1 transduction step.

*E. coli* cells containing the vector BL21(DE3)RNase A will be transformed with pTX0330 and plated out on LB agar supplemented with kanamycin (LBkan) (30 mg/L). pTX0330 is a vector for T7 polymerase promoter driven expression of 'flu' NP protein tagged with six N-terminal histidine residues, generated by cloning NP coding sequence into pET-28a(+) (Novgen Inc.). The N-terminal tag allows for purification of NP by metal chelate chromatography. PTX0330 carries the kanamycin resistance gene kan.

Single colonies will be used to inoculate 25 ml LB supplemented with 30 μg/ml kanamycin (LB kan), and the resulting culture will be grown overnight at 37° C. at 200 rpm. An aliquot of this culture will be used to inoculate 200 ml LBKan. This subculture will be grown to an OD600nm of 1 unit. Six 1.5L aliquots of LBKan will be inoculated with 30 ml of this 200 ml subculture. Protein expression will be induced by the addition of 0.5 mM IPTG (final concentration) for 5 hours. Cells will then be harvested by centrifugation, resuspended in 1% lysis buffer (50 mM NaPO$_4$, 1M NaCl, 0.5% sarkosyl) and frozen at −80° C.

Extraction and Purification

Cells will be thawed on ice in the presence of protease inhibitors (BOEHRINGER MANNHEIM-complete EDTA free protease inhibitor cocktail tablets, 1 tablet/50 ml of cell resuspension). DNase I will be added to a final concentration of 5 mg/ml. The cell pellet will be lysed by homogenization at 30 Kpsi using a single pass in a—CONSTANT SYSTEMS Ltd homogenizer. Alternative homogenization methods can be found in Scopes, supra. The lysate will be subjected to centrifugation at 10,000 g to remove cell debris. Sarkosyl will be added to a final concentration of 0.5% to aid protein solubility and endotoxin removal. Following the addition of 60 ml of 50% Ni-NTA agarose (QIAGEN Inc.), the lysate will be incubated for 1 hour at 4° C. to allow batch binding of the protein to occur.

The bulk of the lysate will be removed from the resin by centrifugation at 200 g. The resin will be resuspended in the remaining lysate and used to pour a PHARMACIA XK 26 column. The column will be washed with 400 ml Wash Buffer (50 mM NaPO$_4$, 1M NaCl, 0.5% sarkosyl, 20 mM imidazole, 10% glycerol). Contaminants will be eluted with a gradient of 0% to 22% 0.5M imidazole in wash buffer. The recombinant NP (rNP) will be eluted with a step gradient of 100% of 0.5% imidazole in wash buffer using a fraction collector.

The appropriate fraction will be analyzed by SDS-PAGE to verify the presence of rNP. The fractions containing the highest concentration of rNP will be pooled (pool 1). Additionally, the fractions containing the lowest concentration of rNP will be pooled (pool 2).

Pooled rNP will be dialyzed into 25 mM Hepes, 0.5% sarkosyl. The protein concentration will be determined by using a BIORAD protein assay. The presence of residual endotoxin will be determined by KQCL assay (BIOWHITTAKER). The presence of residual RNA will be determined according to the methods described in the section entitled Determination of Residual RNA.

EXAMPLE VI

Production and Isolation of pQR163 from *E. coli*

(a) Bacteria, Plasmids and Media

The *Escherichia coli* strain JM107 was used as a plasmid host for the study of bovine pancreatic RNase expression. Control vectors included pUC18, pBR322, pKK223.3 (the vector not containing the RNase gene) and pQR162 (contains two cistron fragment, but in the wrong orientation).

Growth was carried out overnight either in nutrient agar (OXOID nutrient broth solidified with 2% (w/v) bacteriological agar) or in nutrient broth (OXOID). Plates were weekly subcultured in order to maintain plasmid levels, having originally been cultured from glycerol stocks. Single colonies from fresh plates were used to inoculate starter cultures. Growth of cells producing RNase was carried out at 30° C., and controls grown at 37° C.

(b) Induction of pQR163 Cells with IPTG

*E. coli* strain JM107cells transformed with plasmid pQR163 (FIG. 7) were grown in 200 ml of nutrient broth containing 100 μg Ap/ml for 4–5 hours at 28° C. 1 ml aliquots were taken and growth assessed by absorbance readings at 550 nm. Once determined to be in the exponential stage (approx. 0.600 OD$_{550}$) IPTG was added to a final concentration of 0.5 mM Growth was continued overnight and then the cells were harvested.

(c) Plasmid Isolations

Small scale plasmid isolations were performed using QIAGEN kits based on the Birnboim and Doly method (1979). Samples were equally divided into two groups; the spun-down pellets of one group were resuspended in buffer containing RNase, and the other in buffer containing no RNase. Samples of the preparatory stages were taken and loaded onto 1% agarose gels (1M TE buffer, EtBr 0.5 μgml$^{-1}$) along with undigested and EcoRI digested DNA samples.

(d) Quantification of pQR163 and pKK223.3 RNA Concentrations

Midi-scale preparation gels were analysed using a computer software package. Relative intensities and concentrations of λPstI and λHind III markers were used to determine the relative intensities and concentrations of RNA at the cleared lysate and flow stages of pKK223.3 (control) and pQR163.

Results (a) Mini-preparations

Figure 8:
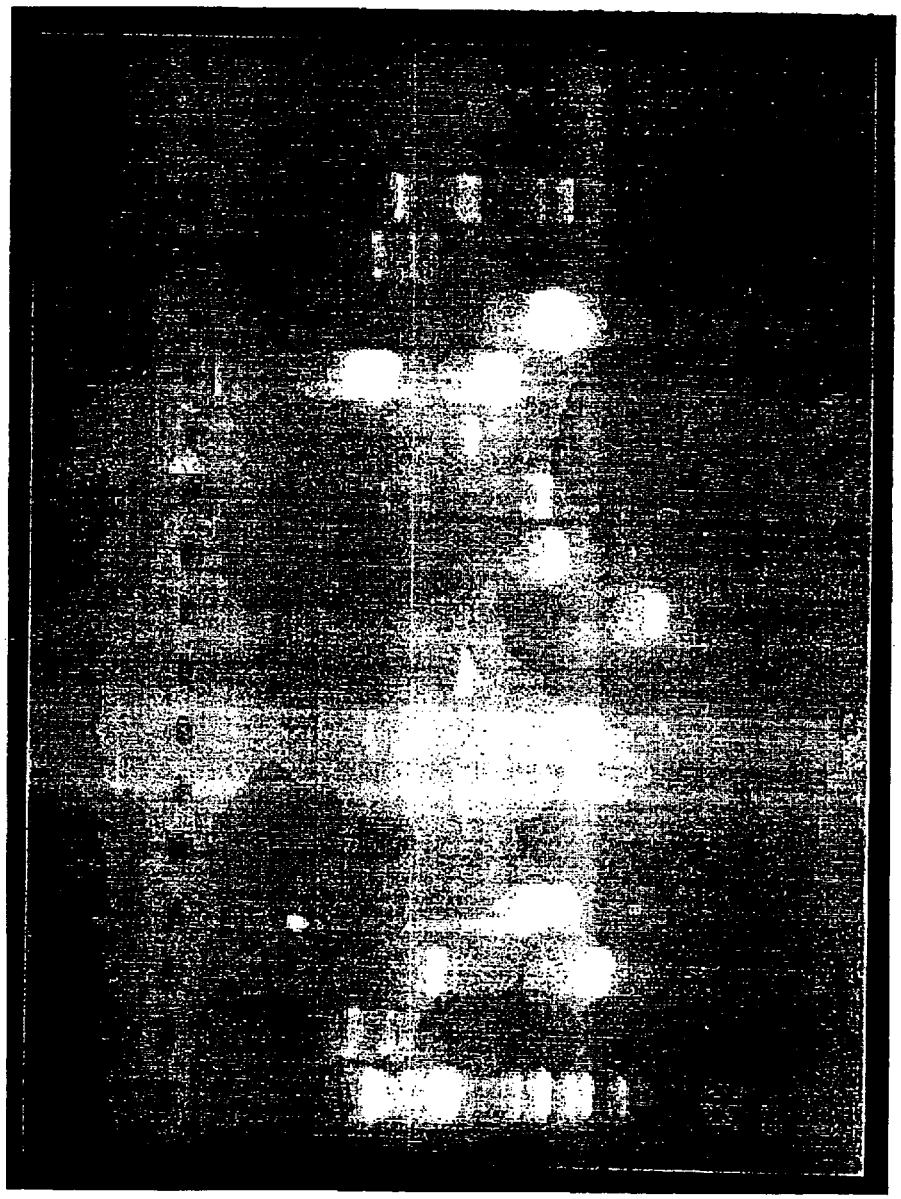
FIG. 8 shows undigested and digested samples of isolated plasmid DNA, with resuspension buffer containing RNase, isolated using a mini-preparatory method. Lanes 1 & 16, 2 & 15 are λPstI and λHind III markers respectively. The first of each of the sample lanes is the undigested sample, and the second lane is the digested sample. Undigested samples were 5 μl DNA and 5 μl of loading buffer. Digested samples contained 5 μl DNA, 1 μl restriction buffer, 1 μl EcoRI and were digested for 2 hours before the addition of 3 μl loading buffer. Lanes 3 & 4 pQR162. Lanes 5 & 6 pQR163. Lanes 7 & 8 pKK223.3. Lanes 9 & 10 pUC18. Lanes 11 & 12 pBR322. Lanes 13 & 14 are the undigested and digested control pUC 19. 5 μl of markers was loaded, and 1 μl of the commercial pUC19 was used.
Figure 9A:
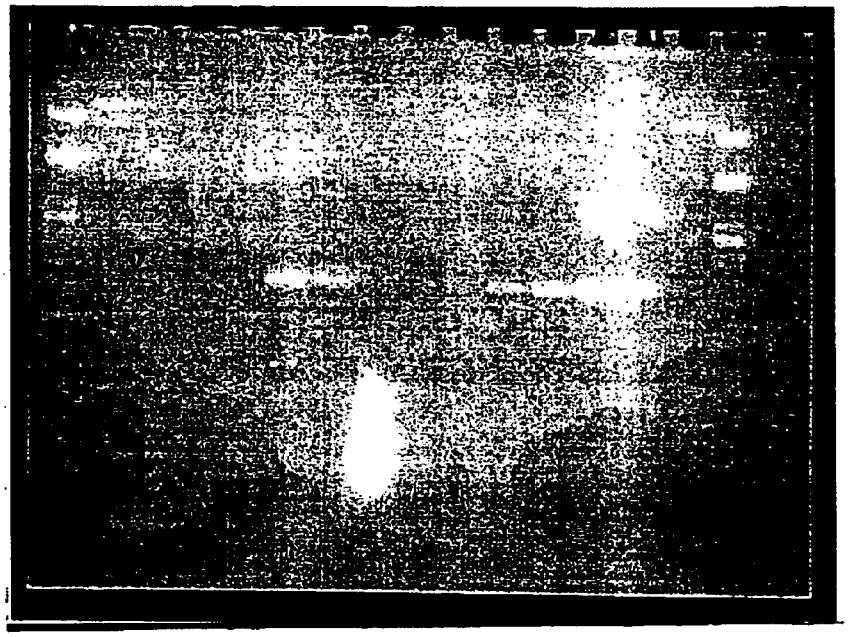
FIG. 9 shows plasmid mini-preparations of flow, washing and eluting stages of (a) vector pKK223.3, which does not contain the RNase gene, (b) pQR163, (c) pQR162, (d) pUC18 and (e) pBR322 using a resuspension buffer with/without RNase. Wells contained a 5 μl stage/DNA sample, 5 μl of sterilised distilled water, and 3 μl of loading buffer. Lanes 1 & 2 and 15 & 16 correspond to λPstI and λHind III respectively (5 μl loaded). Lanes 3–7 correspond to buffer with RNase, and 8–12 correspond to buffer without RNase. Lanes 3 & 8 are flow through samples, lanes 4 & 9 are the first column wash, lanes 5 & 10 are the second column wash, lanes 6 & 7 and 11 & 12 are undigested eluted DNA. Lanes 13 & 14 are undigested commercial pUC18 controls (1 μl loaded).
Figure 9B:
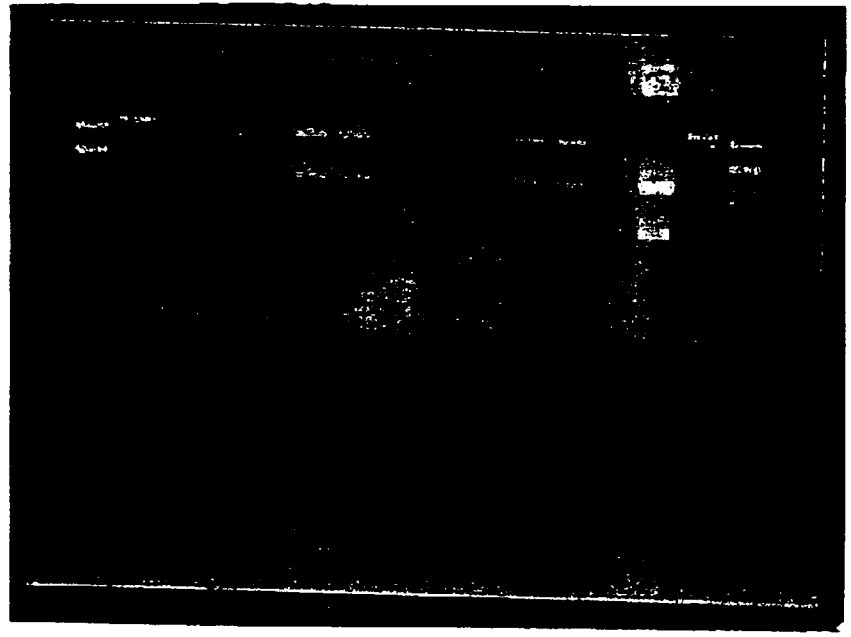
Figure 9C:
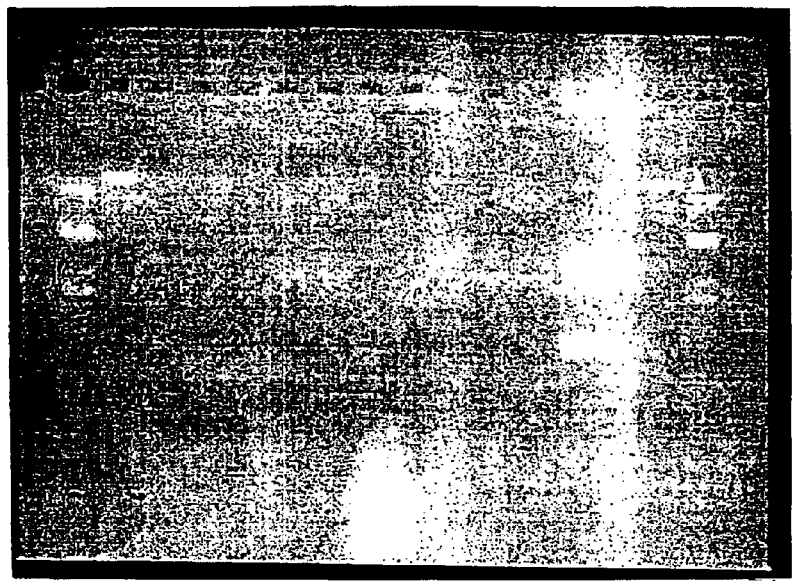
Figure 9D:
Figure 9E:
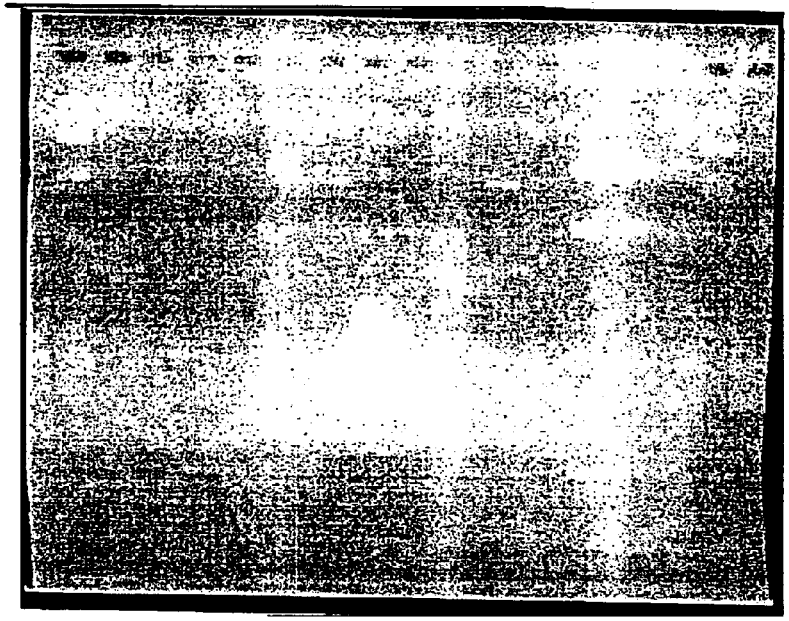

The plasmids pKK223.3, pQR163, pQR162, pUC18 and pBR322 were all purified and the flow, two washes and elution steps retained. The purified plasmid DNA was then digested with EcoRI and run on 1% agarose gels as seen in FIG. 8. The furthest migrating of the two bands seen in the DNA samples is the supercoiled plasmid, and the other is the open circular form of the plasmid. On digestion with EcoRI linear bands are seen indicating that the plasmids do contain sites for the restriction enzyme. pQR162 and pKK223.3 have additional bands; pQR162 contains dimer forms of the plasmid, whereas in the case of pKK223.3 chromosomal DNA may have been loaded into the column due to shearing in the lysis stage of the process. Smearing in the pQR162 digested lane is probably due to foreign DNA falling or being integrated into the gel.

Stages of the mini plasmid preparation were then also loaded onto gels (see FIG. 9). On comparison it can be clearly seen that the presence or absence of RNase in the resuspension buffer has a marked effect on the amount of RNA seen on the gel for pKK223.3. However the effect upon pQR163 is only marginal, with a slight increase in the amount of RNA present in the samples without RNase in the buffer. In both plasmid preparations the majority of RNA is removed by the first washing step of the column.

(b) Midi-preparations

Figure 10:
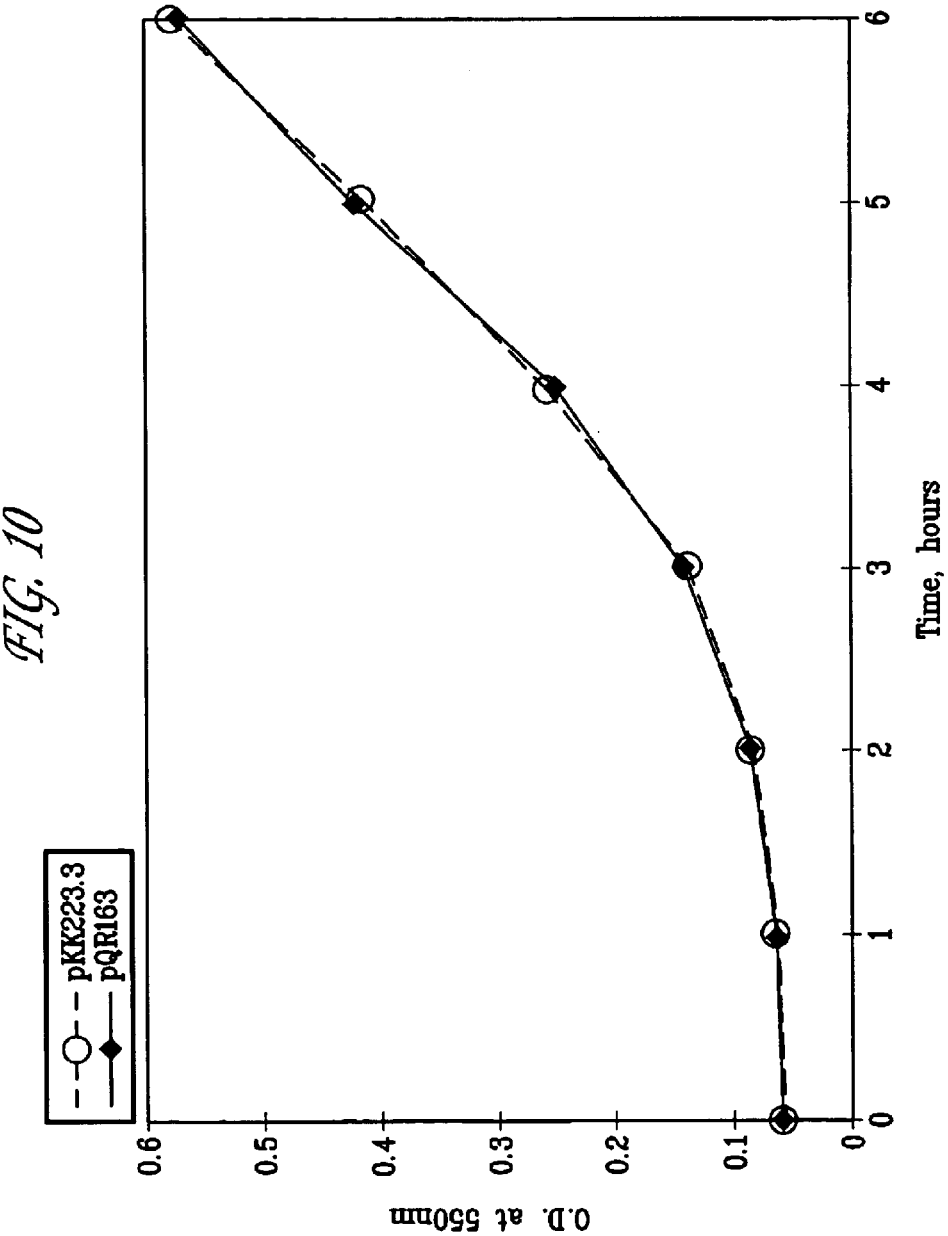
FIG. 10 shows the growth curves of pKK223.3 and pQR163 as determined by optical density readings, prior to induction with IPTG. 1 ml samples were collected every hour and readings at 550 nm were taken against a blank of 1 ml of sterile nutrient broth. Readings were taken at room temperature in 1 ml, 1 cm path cuvets. Exponential growth was determined to be at 0.600 O.D. and samples were then induced with IPTG to a final concentration of 0.5 mM.

Midi-preparations were then undertaken using the control plasmid pKK223.3 and pQR163. Cells were grown in 200 ml of medium in a shake flask for 4–5 hours after inoculation. Growth was monitored using a spectrophotometer at A$_{bs}$ 550 nm (FIG. 10).

Both pKK223.3 and pQR163 are controlled by the tac promoter, and can therefore be induced with IPTG. This growth curve displays closely correlated growth in the two plasmids and indicates when growth is approaching the exponential phase. It is beneficial for the culture to be induced at the exponential phase as this is where there is maximum cell volume before mortality occurs.

Figure 11:
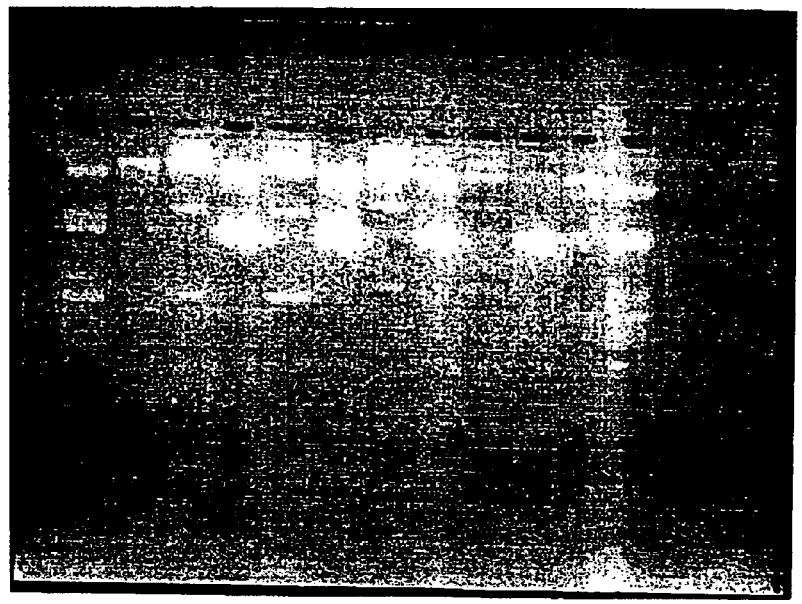
FIG. 11 shows digested and undigested plasmid DNA in the presence/absence of RNase isolated using a midi-isolation method. Lanes 1 & 12 and 2 & 11 are λPstI and λHind III markers respectively (5 μl loaded). The first of each of the DNA lanes is the undigested sample, and the second is the digested sample. Undigested samples were 5 μl DNA and 5 μl loading buffer. Digested samples contained 5 μl DNA, 1 μl restriction buffer, 1 μl EcoRI and were digested for 2 hours before the addition of 3 μl loading buffer. Lanes 3 & 4 pKK223.3 with RNase. Lanes 5 & 6 pKK223.3 without RNase. Lanes 7 & 8 pQR163 with RNase. Lanes 9 & 10 without RNase.

Following induction, the cultures were grown overnight and then the plasmids were isolated using a midi-preparatory method (QIAGEN). Again samples were divided into those with and those without RNase in the resuspension buffer, and digested and undigested DNA run on 1% agarose gels (FIG. 11).

Both pKK223.3 and pQR163 are displaying supercoiled and open circular plasmid bands. The presence of other bands indicates the presence of monomer and dimer forms of the plasmid as seen in lanes 3, 5, 7 and 9. Additionally there are more bands indicating the presence of chromosomal DNA, which may have been caused by exceeding the time of lysis or by rough mixing during the lysis step. All these forms of DNA are seen to linearise when digested with EcoRI. No RNA is seen at this stage of the preparation with or without RNase as the RNA has been removed by the column; it would however effect the efficiency of the column for other contaminant removal.

Figure 12:
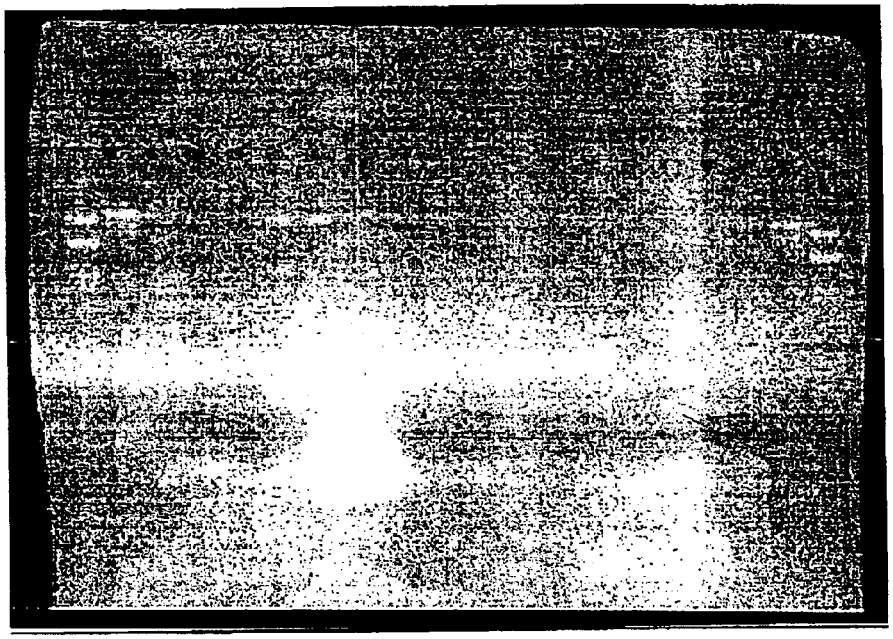
FIG. 12 shows plasmid midi-preparations of clarified lysate, flow, wash and elution stages of pKK223.3 and pQR163 using a resuspension buffer with/without RNase. Wells contained 3 μl of sample, 4 μl of sterilised distilled water and 5 μl of loading buffer. Lanes 1 & 2 and 19 & 20 correspond to λPstI and λHind III respectively (5 μl loaded). Lanes 3–6 and 11–14 correspond to samples pKK223.3 and pQR163 with buffer containing RNase. Lanes 7–10 and 15–18 correspond to pKK23.3 and pQR163 with buffer not containing RNase. Lanes 3, 7, 11 & 15 are clarified lysate stages. Lanes 4, 8, 12 & 16 are flow through stages. Lanes 5, 9, 13 & 17 are wash stages. Lanes 6, 10, 14 & 18 are eluted DNA.

Clarified lysate, wash, flow and elution stages of DNA were then loaded onto a 1% agarose gel (FIG. 12).

RNA levels are seen to be marginally higher in both plasmids with buffers containing RNase in the clarified lysate and flow stages, with pQR163 having a slight degree less RNA than that of pKK223.3. However in samples where no RNase was added to the resuspension buffer, it is clearly seen that pKK223.3 has much greater amounts of RNA than that of the RNase producing plasmid pQR163. Indeed pQR163 contains only marginally more RNA than that of the samples where additional RNase was present. RNA was only seen to be present in the first two plasmid isolation stages, that of the clarified lysate and the flow samples.

c) Computer Analysis

Figure 13:
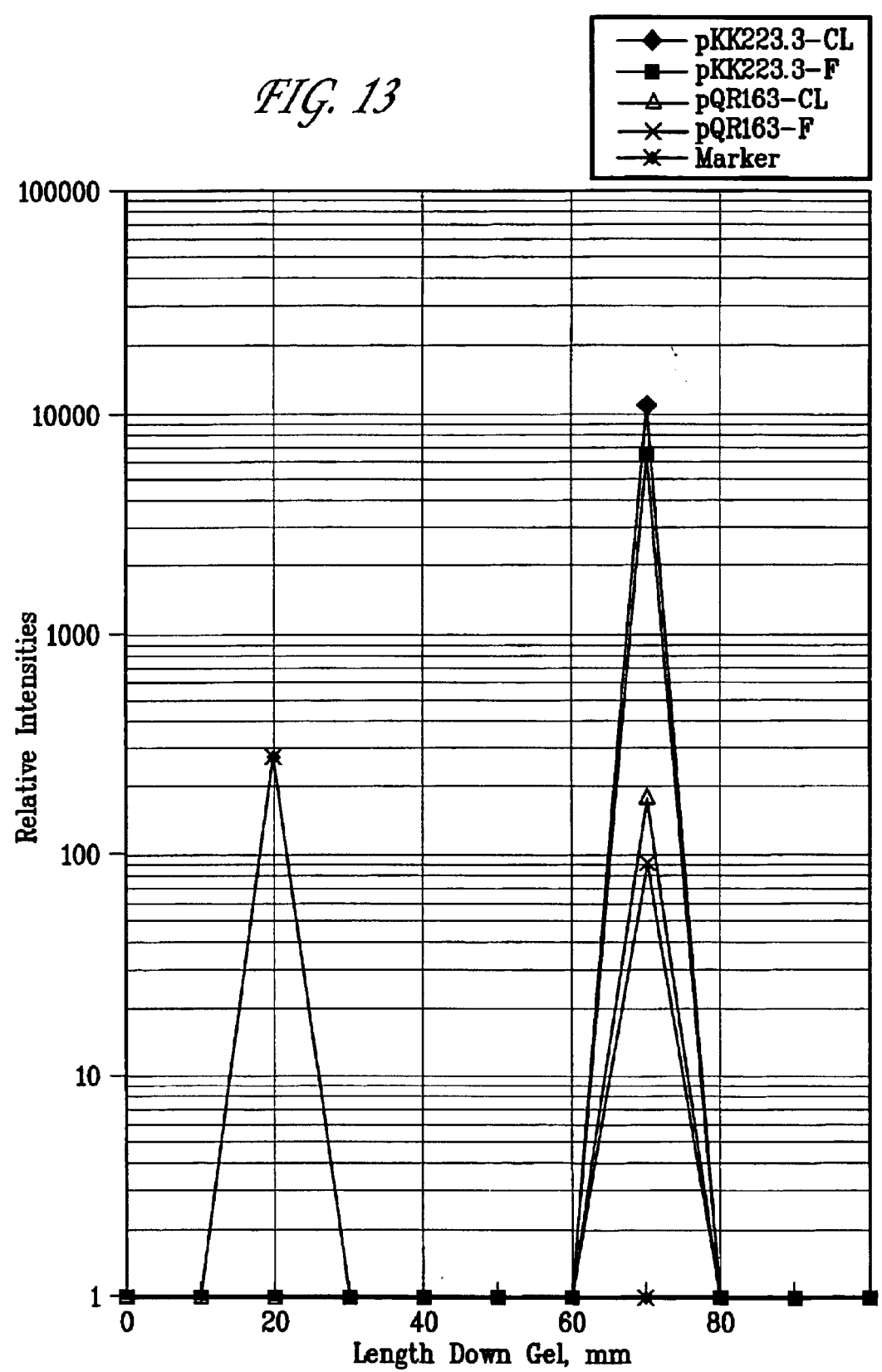
FIG. 13 shows the relative intensities of RNA bands for pKK223.3 and pQR163 for clarified lysate (CL) and flow stages (F) of a midi-preparatory method (QIAGEN) when compared with the second triplet band of λPstI marker.

Computer software was used to relate the intensities of the RNA bands without additional RNase in order to quantify concentrations of RNA on comparison with the second triplet λPstI band (14.32 kb). However, the pQR163 bands had diffused before strictly correct analysis could take place. Therefore the band intensities of the pQR163 bands were related to intensities by use of the photograph; the clarified lysate stage taken to be two-thirds of marker intensity, and the flow stage to be one-third. Due to the huge differences in intensities, the intensities were logged in order to produce a clear graphical record (FIG. 13).

RNA bands displayed higher intensities in both plasmids in the clarified lysate than the flow stages. pKK223.3 were seen to have an average of 64 times (CL=58, F=70) greater intensities of RNA banding than seen in pQR163 which indicates that the RNA is being degraded by the plasmid containing the RNase gene.

Figure 14:
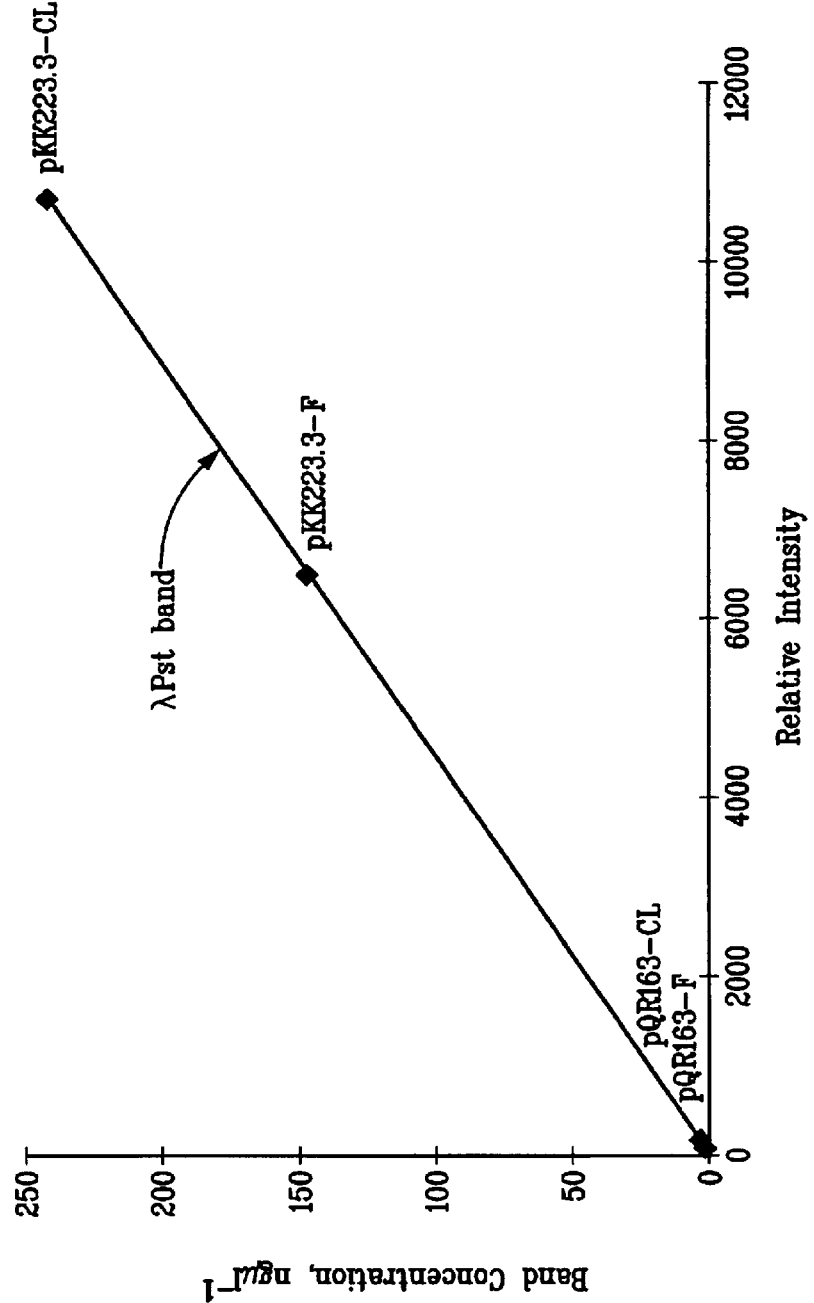
FIG. 14 shows the band concentrations of RNA at cleared lysate (CL) and flow stages (F) of a midi-preparatory process using pKK223.3 and pQR163, as determined by the band concentration of the second triplet band of λPstI marker.

The band concentration of the marker was then determined and used to analyse the RNA band concentrations (FIG. 14).

RNA band concentrations were determined to be 224.0 ng$\mu$l$^{-1}$ (CL) and 147.40 ng$\mu$l$^{-1}$ (F) for pKK223.3, and 4.21 ng$\mu$l$^{-1}$ (CL) and 2.11 ng$\mu$l$^{-1}$ (F) for pQR163. This indicates that the RNase gene in pQR163 is efficiently expressing RNase.

Discussion

Plasmid isolations consistently produced supercoiled and open circular species of plasmid DNA (FIGS. 8, 9, 10, 11 and 12), thereby demonstrating the effectiveness of the technique; supercoiled forms migrated further due to the intense compacting of the molecule whereas open circular forms are found in replicating plasmids. However in some cases other banding patterns were seen, such as monomer and dimer forms of the plasmid and chromosomal DNA (FIGS. 8 & 12). Multimeric forms can be distinguished from chromosomal DNA using restriction digestion; a plasmid displaying many forms will linearise on digestion into one defined band (FIG. 8). Genomic DNA will not linearise following digestion, and a smear will be observed on the gel (FIG. 12). Chromosomal DNA may be produced during lysis and neutralisation steps due to vortexing.

Analysis of RNA band intensities in the absence of additional RNase (FIGS. 13 & 14) revealed that pKK233.3 displayed approximately 58 and 70 times more intense banding for the cleared lysate and flow stages than that seen in pQR163. This is calculated to be a difference in band concentration of approximately 220 ng$\mu$l$^{-1}$ and 145 ng$\mu$l$^{-1}$ for the cleared lysate and flow stages respectively. However, the use of visual guides to determine the intensities of RNA of the pQR163 bands can be inaccurate, hence the emphasis is placed upon approximate values. However the general band differences can clearly be seen (FIG. 12) therefore indicating that the pQR163 is producing effective concentrations of RNase. In fact, little band difference is seen between pQR163 samples with or without RNase, whereas the vector pKK223.3 without the RNase gene shows marked RNA differences (FIGS. 9 & 12). In the future further quantitative methods of computer band analysis will be employed, and band intensities will be related to known concentrations of commercial RNA samples rather than marker bands.

The small-scale plasmid isolations used here consist of three basic steps: (i) preparation and clearing of a bacterial lysate, (ii) adsorption of DNA onto the column membrane and (iii) the washing and elution of the plasmid DNA. The columns use a silica-gel membrane to selectively adsorb plasmid DNA in high-salt buffer conditions and to elute in low-salt buffers (QIAGEN). RNA was seen to be present in the cleared lysate and flow stages of the plasmid isolation procedures (FIGS. 9 and 12). Subsequent steps revealed no RNA due to washing of the column removing contaminants such as RNA, cellular proteins and metabolites as they are not selectively adsorbed. However the columns are only detailed to be efficient when using "optimised buffers" (QIAGEN) i.e. those containing RNase A. Therefore samples without the addition of RNase in the resuspension buffer produced high concentrations of RNA in pKK223.3 samples, and may also reduce the efficiency of the chromatography steps by competing with DNA for the binding sites.

Hence using a plasmid containing a gene for RNase production prevents the need for separate RNase additions, yet the efficiency of the column separation is still maintained. Accordingly, a safe pharmaceutical grade pure plasmid product can be isolated using the methods of the present invention.

EXAMPLE VII

Strategy for the Chromosomal Insertion of RNaseA

This strategy is an alternative strategy for inserting an RNase gene into the chromosome of a host strain and is in addition to those described in the previous section entitled Integration of An RNase Gene Into The Chromosome of the E. coli. Host Strain.

The trc-RNaseA fusion from pQR163 was excised as a BamHI fragment (775 bp) and blunt-ended by 5' overhang fill-in with the Klenow fragment of DNA polymerase I. The plasmid pN1D274Ekan1 was cut with BbsI, which removed a region including most of the lacI$^{qs}$ coding sequence, leaving an 8651 bp linear plasmid. This was blunt-ended by 5' overhang fill-in and dephosphorylated using calf intestinal alkaline phosphatase (CIAP) to prevent recircularisation in the absence of an insert. Filling-in of 3' recessed DNA fragment ends with Klenow polymerase and dephosphorylation with CIAP was carried out as described in the NEW ENGLAND BIOLABS catalogue (1998/1999), NEW ENGLAND BIOLABS Inc., 32 Tozer Road, Beverly, Mass., USA. The blunted BamHI fragment containing the trc-RNaseA fusion is ligated into pN1D274Ekan1 to form the insertion plasmid: pRNaseA. Construction of pRNaseA is illustrated in FIG. 15.

Calcium-competent JM107 cells (endA1, thi, gyrA96, hsdR17 ($r_k^-$, $m_k^+$), relA1, supE44, Δ(lac-proAB), [$F^1$ traD36, proAB, lacI$^q$ZΔM15]) are transformed with the plasmid pTP223, selecting transformants on LB agar plates containing 12 μg μl$^{-1}$ tetracycline (Tet). pTP223 contains tet and the λ red recombination functions bet and exo, and the RecBCD-inhibiting λ gam (Murphy 1997, J. Bacteriol. 180: 2063–2071). A RecA$^+$ strain is chosen as recombination efficiency is higher using this system. Calcium-competent cells are prepared and transformations carried out as described in Ausubel et al. (Current Protocols in Molecular Biology, supra).

pRNaseA is linearised using enzymes that cut only in the pUC18 backbone, such as AatII, NdeI, SacI and XmnI. Calcium-competent JM107(pTP223) are prepared and transformed with linear pRNaseA, selecting recombinants on LB agar plates containing 50 μg μl$^{-1}$ kanamycin. The resulting strain is designated JMRNaseA.

For testing for RNaseA activity by plate assay and agarose gel electrophoresis, JMRNaseA(pTP223) and JM107 (pTP223) (negative control) are grown to mid-log phase in LB broth with Tet and induced by the addition of 0.5 mM IPTG at 2 hours prior to harvesting. Controls are performed without the addition of IPTG. The RNase plate assay is performed as follows. Onto an LB agar plate with Tet there is spotted 10 μl of each culture, along with 0.1 μg commercial RNaseA in 10 μl H$_2$O. This is incubated at 37° C. overnight, then overlaid with 6.0 ml soft agar containing 0.3% (w/v) bakers' yeast in 11.0 mM EDTA and incubated for a further 4 hours. The plate is then developed by the addition of 10 ml of 1.0 M HCl and photographed. The expected results are displayed in Table 1. For agarose gel electrophoresis, QIAGEN minipreparations are performed on the cultures (following manufacturer's protocol) with and without the addition of RNaseA to the cell resuspension buffer (100 μg ml$^{-1}$). Then 5 μl of each plasmid prep is loaded into a 0.8% agarose gel and electrophoresis takes place at 5 V cm$^{-1}$. The gel is post-stained with Sybr Green dye and visualised on a MOLECULAR DYNAMICS FLUORIMAGER at 545 nm to detect RNA. The expected results are summarised in Table 2.

TABLE 1

RNaseA activity as determined by an RNase plate assay.

| Control | RNaseA activity | |
|---|---|---|
| 0.1 μg RnaseA | + | |
| Strain | IPTG added | No IPTG |
| JM107(pTP223) | − | − |
| JMRNaseA(pTP223) | + | − |

TABLE 2

Detecting RNA by agarose gel electrophoresis following plasmid preparation.

| | RNA present | |
|---|---|---|
| Strain | RNaseA added | No RNaseA |
| JM107(pTP223) | − | + |
| JMRNaseA(pTP223) | − | − |

EXAMPLE VIII

Figure 19B:
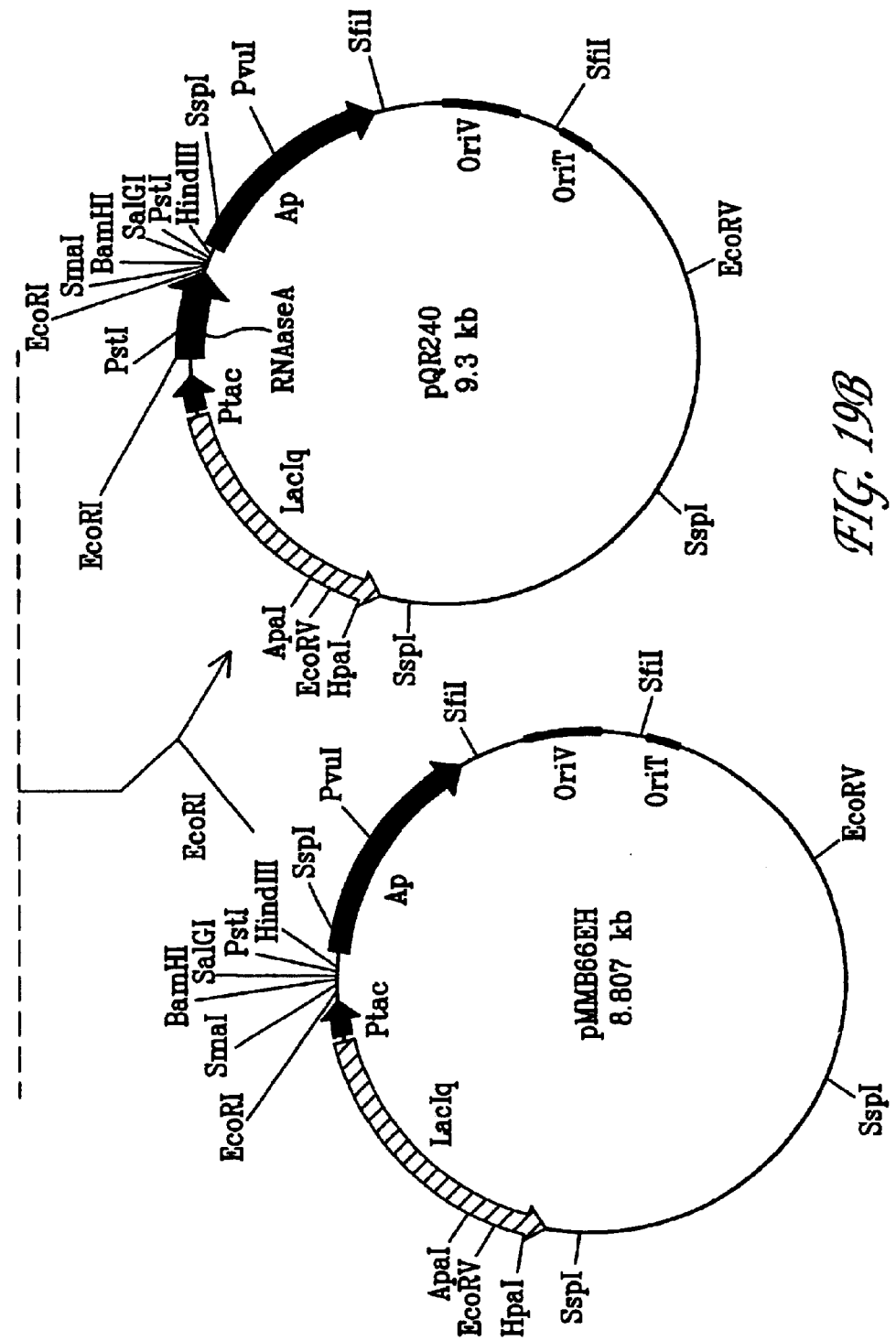
FIG. 19 shows the strategy for cloning the RNaseA gene into pMMB66EH.

Using a Two-plasmid System to Demonstrate the Activity of Periplasmically-localised RNaseA The therapeutic plasmid pTX0161 is used as a form of cancer chemotherapy, gene directed enzyme prodrug therapy, to promote the crosslinking of DNA in affected cells. This is achieved by the activation of E.coli B nitroreductase enzyme by the prodrug CB1954 (Drabek, D., Guy, J., Craig, R. and Grosveld, F. 1997 The expression of bacterial nitroreductase in transgenic mice results in specific cell killing by the prodrug CB1954 *Gene Therapy* 4:93–100.). To test the RNase activity in a strain carrying pTX0161 (ColEI ori), the RNaseA gene from low-copy number plasmid pQR163 (also ColEI ori) is cloned into another plasmid with a compatible origin, namely pMMB66EH. PMMB66EH is an 8.8 kb low copy number plasmid conferring ampicillin resistance. Expression of RNaseA activity from this vector allows the determination of the effect of decreasing copy number prior to integrating into the genome of a host cell. The strategy for cloning the RNaseA gene into pMMB66EH is shown in FIG. 19 and is described as follows:

1. Obtaining RNaseA ORF, including native signal sequence, from pQR163 via digestion with EcoRI, yielding a fragment <500 bp.

2. Isolating RNaseA fragment via preparative 1% agarose gel.

3. PMMB66EH is digested with EcoRI, and subsequently the 5' phosphate removed by treating with calf intestinal alkaline phosphatase.

4. Ligation of RNaseA gene of the EcoRI fragment into pMMB66EH linearised with EcoRI.

5. Transformation of competent *E. coli* JM 107 with construct and selecting for transformants on nutrient agar plates containing ampicillin.

6. Correct clones are screened by miniprepping DNA from cultures grown from transformant colonies digested with EcoRI to confirm the presence of the insert and PstI to determine orientation.

Ensuring correct orientation and expression of the insert by re-plating transformants onto buffered nutrient agar (0.1M Tris Cl, pH7.0) containing yeast RNA. RNase activity can be detected by the addition of 2M HCl to the plates following overnight growth. Clear areas are present surrounding colonies expression RNase activity, whilst areas of RNA will produce a white precipitate after the addition of HCl.

Figure 16:
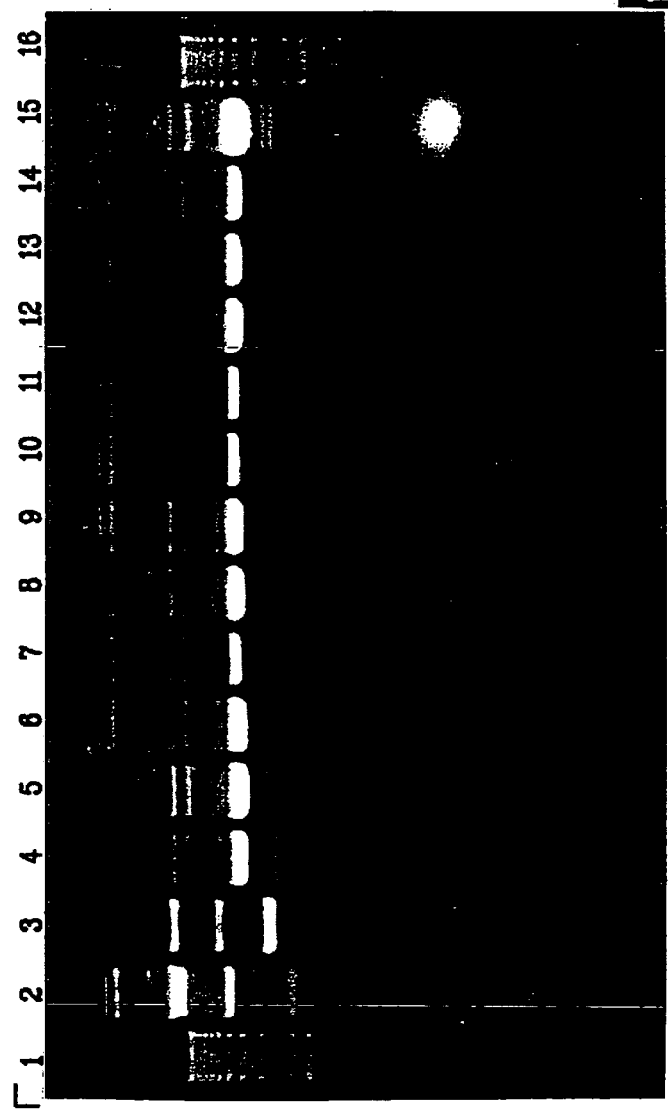
FIG. 16 shows an agarose gel electrophoresis of plasmid minipreparations of clones derived from the transformation of pQR163 into DH1(pTX0161): Lanes 1 & 16: 1 kb marker, Lane 2: pMMB66EH; Lane 3: pQR163 control; Lanes 4–15: Clones 1–12 of DH1(pTX0161)(pQR163).

However, as both pQR163 and pTX0161 carry different antibiotic resistance genes (pQR163 has amp, pTX0161 has tet), it was possible to maintain pQR163 and pTX0161 in the same cell provided the medium was supplemented with ampicillin and tetracycline in spite of the fact that both contain ColEI derived ori of replication.

pQR163 was transformed into calcium-competent DH1 (PTX0161). Colonies were obtained on the double antibiotic selection plates. Twelve of these were isolated and the DNA extracted by a QIAGEN minipreparation. The result showed (FIG. 16) that pQR163 and pTX0161, despite being incompatible plasmids, were coexisting in the host cell.

Figure 17:
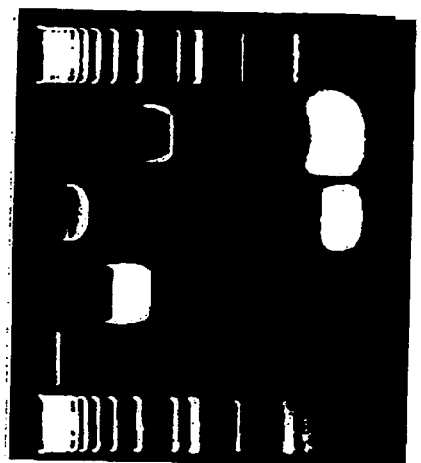
FIG. 17 shows an agarose gel electrophoresis of plasmid minipreparations from DH1(pTX0161)(pQR163) and DH1 (pTX0340): Lanes 1 and 6: 1 kb marker; Lane 2: DH1 (pTX0161)(pQR163)+RNaseA; Lane 3: DH1(pTX0340)+ RNaseA; Lane 4: DH1(pTX0161)(pQR163); Lane 5: DH1 (pTX0340).

To determine whether the RNaseA gene was still functional, a clone of DH1(pTX0161)(pQR163) was analysed along with a control of DH1(pTX0340), which does not contain an RNase gene. These were cultured in LB broth with their corresponding antibiotics to mid-log phase, then IPTG was added to induce the RNaseA gene and incubation was continued for a further 1.5 hours. Plasmid DNA extracts with and without RNaseA in the miniprep solutions (as described previously) were subjected to agarose gel electrophoresis, staining with ethidium bromide and were visualised on a UV transilluminator. There is evidence of RNase activity in the form of a smaller RNA band in DH1(PTX0161)(pQR163) than is present in the DH1 (pTX0340) control (FIG. 17).

Figure 18:
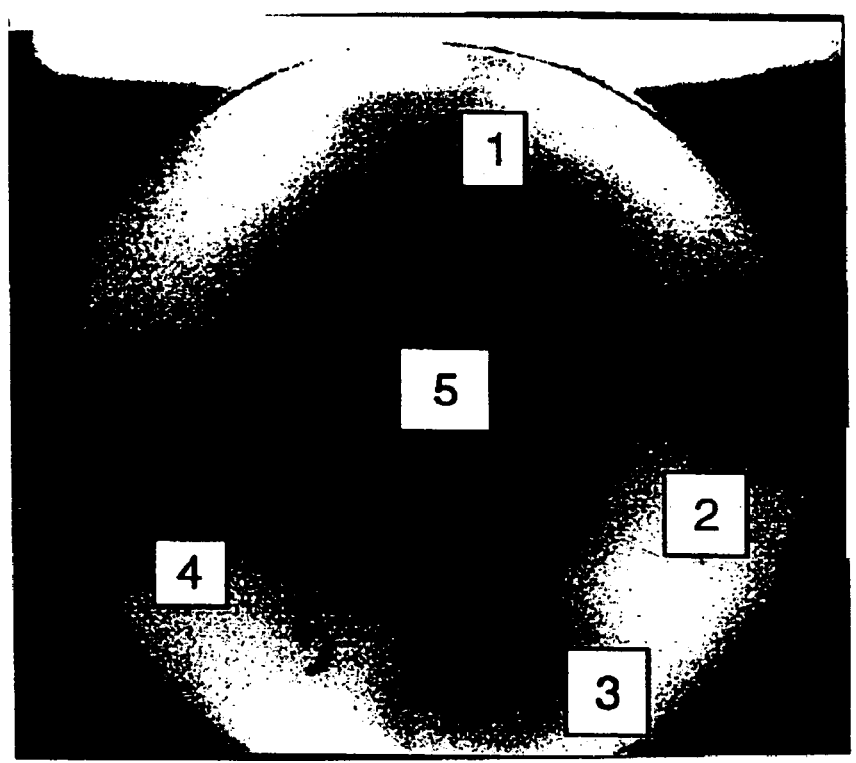
FIG. 18 shows an RNA plate assay to detect RNaseA activity: 1: pMMB66EH (negative control); 2–4: DH1 (pTX0161)(pQR163) clones 1–3; 5: 10 μg RNaseA (positive control).

To illustrate the activity of RNaseA in DH1(pTX0161) (pQR163), a plate assay was performed as described previously. There were zones of RNA digestion surrounding the test colonies and the bovine RNaseA positive control, but none surrounding the DH1(pMMB66EH) negative control (FIG. 18).

Cellular Components Useful According to the Invention

Proteins Useful According to the Invention

Proteins useful according to the methods of the invention include but are not limited to proteins that are useful according to the invention, such as receptors, enzymes, ligands, regulatory factors, and structural proteins. Therapeutic proteins also include nuclear proteins, cytoplasmic proteins, mitochondrial proteins, secreted proteins, plasmalemma-associated proteins, serum proteins, viral antigens, bacterial antigens, protozoal antigens and parasitic antigens.

Therapeutic proteins useful according to the invention also include lipoproteins, glycoproteins and phosphoproteins. Proteins or polypeptides which can be expressed using the methods of the present invention include hormones, growth factors, neurotransmitters, enzymes, clotting factors, apolipoproteins, receptors, drugs, oncogenes, tumor antigens, tumor suppressors, structural proteins, viral antigens, parasitic antigens and bacterial antigens. Specific examples of these compounds include proinsulin, growth hormone, dystrophin, androgen receptors, insulin-like growth factor I, insulin-like growth factor II, insulin-like growth factor binding proteins, epidermal growth factor TGF-α, TGF-β, PDGF, angiogenesis factors (acidic fibroblast growth factor, basic fibroblast growth factor and angiogenin), matrix proteins (Type IV collagen, Type VII collagen, laminin), phenylalanine hydroxylase, tyrosine hydroxylase, oncogenes (ras, fos, myc, erb, src, sis, jun), E6 or E7 transforming sequence, p53 protein, Rb gene product, cytokine receptor, Il-1, IL-6, IL-8, viral capsid protein, and proteins from viral, bacterial and parasitic organisms which can be used to induce an immunologic response, and other proteins of useful significance in the body.

The compounds, which can be incorporated, are only limited by the availability of the nucleic acid sequence for the protein or polypeptide to be incorporated. One skilled in the art will readily recognize that as more proteins and polypeptides become identified they can be integrated into the non-viral vector of choice, transfected according to the method of the present invention and expressed in a mammalian tissue, including human tissue.

DNA Sequences Useful According to the Invention
1. Genes Encoding Toxins

Examples of genes useful in the invention include those encoding such agents including but not limited to genes encoding diphtheria toxin, Pseudomonas exotoxin, cholera toxin, pertussis toxin, etc., as follows. Diphtheria toxin-IL2 fusions for inhibition of HIV-1 infection (Zhang et al., 192, Jour. Acquired Immune Deficiency Syndrome 5:1181); Diphtheria toxin A chain for inhibition of HIV viral production (Harrison et al., 1992, AIDS Res. Hum. Retro. 8:39 and Curel et al., 1993, Hum. Gene Ther. 4:71); Diphtheria toxin A chain-liposome complexes for suppression of bovine leukaemia virus infection (Kakidani et al., 1993, Microbiol. Immunol. 37:713); Diphtheria Toxin A chain gene coupled with immunoglobulin enhancers and promoters for B-cell toxicity (Maxwell et al., Cancer Res., 1991, 51:4299); Tat- and Rev-activated expression of a diphtheria toxin A gene (Harrison, 1991, Hum. Gene Ther. 2:53); Diphtheria toxin-CD4 fusion for killing of HIV-infected cells (Auilo et al., 1992, Eur. Mol. Biol. Org. Jour. 11:575).

Other toxins which are useful according to the invention include but are not limited to the following. Conditionally toxic retroviruses are disclosed in Brady et al., 1994, Proc. Nat. Aca. Sci. 91:365 and in Caruso et al, 1992, Bone Marrow Transplant, 9:187. Toxins against EBV infection are disclosed in Harris et al., 1991, Cell. Immunol. 134:85, and against poliovirus in Rodriguez et al., 1992, Jour. Virol. 66:1971. Toxins against influenza virus are disclosed in Bron et al., 1994, Biochemistry 33:9110.

2. Genes Encoding Immunoactive Agents

Another agent useful according to the invention includes immunoactive agents, i.e., agents that combat viral infections or production by activating an immune response to the virus. Such agents include but are not limited to cytokines against viruses in general (Biron, 1994, Curr. Opin. Immunol. 6:530); soluble CD4 against SIV (Watanabe et al., 1991, Proc. Nat. Aca. Sci. 88:126); CD4-immunoglobulin fusions against HIV-1 and SIV (Langner et al., 1993, Arch. Virol. 130:157); CD4(81–92)-based peptide derivatives against HIV infection (Rausch et al., 1992, Biochem. Pharmacol. 43:1785); lympho-cytotoxic antibodies against HIV infection (Szabo et al., 1992, Acta Virol. 38:392); IL-2 against HIV infection (Bell et al., 1992, Clin Exp. Immunol. 90:6; and anti-T cell receptor antibodies against viruses in general (Newell et al., 1991, Ann. N.Y. Aca. Sci. 636:279).

3. Genes Encoding Anti-Viral Drugs

Another anti-viral agent useful according to the invention includes drugs having anti-viral activity and which are the direct product of a gene or are a product of a gene encoding a precursor of the drug, the drug then being synthesized by a biosynthetic pathway in the cell. Targets of drug intervention in the replicative cycle of, for example, a retrovirus, include (i) binding and entry, (2) reverse transcriptase, (3) transcription and translation, and (4) viral maturation and budding. Representative inhibitors of viral binding and entry for HIV include recombinant soluble CD4, immunoadhesions, peptide T, and hypericin. Nucleoside reverse transcriptase inhibitors include zidovudine, didanosine, zalcitabine, and starudine. Foscarnet, tetrahydroimidazobenzodiazepinethione compounds, and nevirapine are some non-nucleoside reverse transcriptase inhibitors. Inhibitors of transcription and translation include antagonists of the TAT gene and GLQ223. Castanospermine and protease inhibitors interfere with viral budding and maturation. Such drugs include but are not limited to nucleoside or nucleotide analogs and products of a cellular biosynthetic pathway such as described in Harrell et al., 1994, Drug Metab. Dispos. 22:124 (deoxy-guanine); Fillon et al., 1993, Clin. Invest. Med. 16:339 (dauno-rubicin); Ohrvi et al., 1990, Nucleic Acids Symp. 26:93 (anti-viral nucleosides); Hudson et al., 1993, Photochem. Photobiol. 57:675 (thiarubines); Salhany et al., 1993, Jour. Biol. Chem. 268:7643 (pyridoxal 5'-phosphate); Damaso et al., 1994, Arch. Viral. 134:303 (cyclosporin A); Gallicchio et al., 1993.

Int. Jour. Immunol. 15:263 (dideoxynucleoside drugs); and Fiore et al., 1990, Biol. Soc. Ital. Biol. Sper. 66:601 (AZT).

4. Genes Encoding Proteins or Enzymes Useful for the Treatment of Patients by Gene Therapy Genes encoding proteins or enzymes useful for the treatment of patients by gene therapy include genes encoding β-glucocerbrosidase for Gaucher's disease, Factor XIII and IX for hemophilia and prodrug activating enzymes for use in prodrug treatments (e.g. bacterial nitroreductases for use in gene directed enzyme prodrug therapy (GDEPT)).

Vectors Useful According to the Invention

Vectors useful according to the invention include a vector that possesses the following characteristics:

i) High Copy Number Bacterial Origin of Replication.

Vectors having relatively high copy number, i.e., in the range of 20–40 copies/cell up to 1000–2000 copies/cell, are especially useful according to the invention. For example, a vector that includes the pUC origin of replication is preferred according to the method of the invention. The pUC origin of replication permits more efficient replication of plasmid DNA and results in a tenfold increase in plasmid copy number/cell over, e.g., a pBR322 origin. The resulting high copy number greatly increases the ratio of plasmid DNA to chromosomal DNA, RNA, cellular proteins and co-factors, improves plasmid yield, and facilitates easier downstream purification.

ii) Small and Stable Vector Backbone.

It is preferred according to the invention that the backbone of a vector used according to the methods described herein be small, i.e., less than 5 kb, and preferably 1–3 kb. The term "vector backbone" refers to the bacterial DNA necessary to maintain and propagate the vector in a bacterial host. Vectors of the invention, which include both backbone and insert, will be on the order of 15–50 kb in size, or even larger. Thus, a vector backbone useful in the invention will be capable of carrying inserts of approximately 10–50 kb or larger. The insert may include DNA from any organism, but will preferably be of mammalian origin, and may include, in addition to a gene encoding a therapeutic protein, regulatory sequences such as promoters, polyadenylation sequences, enhancers, locus control regions, etc. The gene encoding a therapeutic protein may be of genomic origin, and therefore contain exons and introns as reflected in its genomic organization, or it may be derived from complementary DNA.

The vector should also be stably inherited; that is, the vector backbone preferably contains no intrinsically unstable elements prone to rearrangement, deletion, etc, such as transposons, and is stably inherited in the presence of the selective agent.

Useful vectors according to the invention include pEAβGlu, pUC18/19tetΔAmp, pTX0161, pUC19tet, pGL2RSV, pGL2RSVluc, pAI6tet and pCD2tatRZfull.

iii) Polylinker Suitable for the Insertion of Therapeutic Genes and Regulatory Sequences.

Vectors useful according to the invention include a polylinker comprising a variety of restriction sites that are useful in cleaving the vector and incorporating therapeutic genes.

iv) Absence of Other Bacterial Protein Genes.

It is preferred according to the invention that no other bacterial genes are carried on the vector backbone. Absence of other bacterial genes minimizes the possibility of a patient developing an immune response to a foreign gene or its encoded product, where the gene is present and/or expressed in the patient's cells, which have been targeted with the therapeutic vector. Other bacterial genes expressed by host strain during fermentation results in a metabolic burden in the host and reduce the biomass and plasmid yields.

v) Selective Marker Gene.

Vectors useful according to the invention may include a gene encoding a selectable marker, e.g., an antibiotic resistance gene such as the bacterial tetracycline resistance gene. Incorporation of the tetracycline resistance gene permits the use of tetracycline as a selective agent in the plasmid preparation procedure according to the invention. One advantage to the use of a tetracycline resistance gene is that tetracycline is not degraded in $E.$ $coli$, and therefore more tetracycline does not have to be added during fermentation. In addition, the tetracycline resistance gene is preferred over a gene encoding ampicillin resistance because tetracycline is prescribed less often as an antibiotic in a clinical setting, and adverse responses to tet are less frequent than for amp and other β-lactam antibiotics.

Dosage, Mode of Administration and Pharmaceutical Formulations

The invention encompasses methods of removing RNA from preparations of cellular components.

A pharmaceutical composition comprised of a cellular component produced from a host cell that also produces an RNase may be prepared from preferably $10^5$–$10^8$ host cells and more preferably from $10^6$–$10^7$ host cells. A pharmaceutical composition comprised of a cellular component produced from a host cell that has been co-cultured with a different host cell that produces an RNase may be prepared from preferably $10^5$–$10^8$ of each respective host cell and more preferably from $10^6$–$10^7$ of each host cell. In the latter embodiment the two host cells are preferably present in the culture in a 1:1 ratio or are mixed at the point of lysis in a 1:1 ratio.

Cellular components described herein may be prepared as injectables, either as liquid solutions or suspensions; solid forms suitable for solution in or suspension in, liquid prior to infection can also be prepared. The preparation can also be emulsified, or the cellular component encapsulated in liposomes. The term "pharmaceutically acceptable carrier" refers to a carrier that does not cause an allergic reaction or other untoward effect in subjects to whom it is administered. Suitable pharmaceutically acceptable carriers include, for example, one or more of water, saline, phosphate buffered saline, dextrose, glycerol, ethanol, or the like and combinations thereof. In addition, if desired, the composition can contain minor amounts of auxiliary substances such as wetting or emulsifying agents, pH buffering agents, and/or adjuvants, which enhance the effectiveness of the vaccine. Examples of adjuvants which may be effective include but are not limited to: aluminium hydroxide, N-acetyl-muramyl-L-threonyl-D-isoglutamine (thr-MDP), N-acetyl-nor-muramyl-L-alanyl-D-isoglutamine (CGP 11637, referred to as nor-MDP), N-acetylmuramyl-L-alanyl-D-isoglutaminyl-L-alanine-2-(1'-2'-dipalmitoyl-s n-glycero-3-hydroxyphosphoryloxy)ethylamine (COP) 19835A, referred to as MTP-PE), and RIBI, which contains three components extracted from bacteria, monophosporyl lipid A, trehalose dimycolate and cell wall skeleton (MPL+TDM+CWS) in a 2% squalene/Tween 80 emulsion. Other examples of adjuvants include DDA (dimethyldioctadecylammoniun bromide), Freund's complete and incomplete adjuvants and QuilA.

Cellular components of the invention can be administered parenterally, by injection, for example, either subcutaneously or intramuscularly. Additional formulations which are suitable for other modes of administration include suppositories, and in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%–2%. Oral formulations include such normally employed excipients as, for example, pharmaceutical grades of mannitol, lactose, starch magnesium stearate, sodium saccharine, cellulose, magnesium carbonate, and the like. These compositions take the form of solutions, suspensions, tablets, pills, capsules, sustained release formulations or powders and contain 10%–95% of active ingredient, preferably 25–70%.

The foregoing examples are meant to illustrate the invention and not to limit it in anyway. Other applications and modifications are within the spirit and scope of the invention as herein disclosed and will be readily apparent to those skilled in the art.

Other Embodiments

Other embodiments are within the following claims.

All references cited herein are hereby incorporated by reference in their entireties.

What is claimed is:

1. A method of preparing a substantially RNA-free cellular component comprising:
   a) culturing a microbial cell producing the cellular component and an RNase, wherein said RNase is secreted into the periplasm of said cell;
   b) lysing said cell to produce a cell lysate, wherein said cell lysate comprises said cellular component and sufficient RNase activity to degrade substantially all of the RNA present in said cell lysate;
   c) incubating said cell lysate to allow said RNase to digest said RNA; and
   d) isolating said cellular component.

2. A method of preparing a substantially RNA-free cellular component comprising:
   a) culturing a microbial cell producing said cellular component and an RNase in a medium, wherein said cellular component and said RNase are secreted out of the cytoplasm of the cell into the medium and further wherein said medium contains sufficient RNase activity to degrade substantially all of the RNA present in said medium; and
   b) isolating said cellular component.

3. The method of claim 2 further comprising incubating said medium to allow said RNase to digest said RNA.

4. A method of preparing a substantially RNA-free cellular component comprising:
   a) culturing a microbial cell producing the cellular component and an RNase, wherein said cellular component is secreted out of the cytoplasm of the cell and said RNase is secreted into the periplasm of said cell;
   b) lysing said cell to produce a cell lysate, wherein said cell lysate contains said cellular component and sufficient RNase activity to degrade substantially all of the RNA present in said cell lysate;
   c) incubating said cell lysate to allow said RNase to digest said RNA; and
   d) isolating said cellular component.

5. The method according to claim 1, 2, or 4, wherein said cellular component is selected from the group consisting of DNA, protein, and carbohydrate.

6. The method according to claim 1, 2, or 4, wherein said RNase is encoded by a gene that is integrated into the genome of the cell producing the RNase.

7. The method according to claim 1, 2, or 4, wherein said RNase is non-specific.

8. The method according to claim 1, 2, or 4, wherein said RNase is RNase A, RNase M or RNase I.

9. The method according to claim 1, 2, or 4, wherein expression of said RNase is transcriptionally, translationally, or post-translationally regulated.

10. The method according to claim 1, 2, or 4, wherein said RNase is overproduced.

11. The method of according to claim 1, 2, or 4, wherein expression of said RNase is inducible.

12. The method according to claim 1, 2, or 4, wherein expression of said RNase is constitutive.

* * * * *

SEQUENCE LISTING

<160> NUMBER OF SEQ ID NOS: 8

<210> SEQ ID NO 1
<211> LENGTH: 30
<212> TYPE: DNA
<213> ORGANISM: Unknown
<220> FEATURE:
<223> OTHER INFORMATION: Description of Unknown Organism: Primers

<400> SEQUENCE: 1
ctcgaattca atgttcttgg aggatgattg                                    30

<210> SEQ ID NO 2
<211> LENGTH: 29
<212> TYPE: DNA
<213> ORGANISM: Unknown
<220> FEATURE:
<223> OTHER INFORMATION: Description of Unknown Organism: Primers

<400> SEQUENCE: 2
tacgaattcg gccttaggta gagacctac                                     29

<210> SEQ ID NO 3
<211> LENGTH: 30
<212> TYPE: DNA
<213> ORGANISM: Unknown
<220> FEATURE:
<223> OTHER INFORMATION: Description of Unknown Organism: Primers

<400> SEQUENCE: 3
ggtcctgggg tgattattta cggctgtggc                                    30

<210> SEQ ID NO 4
<211> LENGTH: 30
<212> TYPE: DNA
<213> ORGANISM: Unknown
<220> FEATURE:
<223> OTHER INFORMATION: Description of Unknown Organism: Primers

<400> SEQUENCE: 4
gtttaactca catgatgata ctgactgttg                                    30

<210> SEQ ID NO 5
<211> LENGTH: 28
<212> TYPE: DNA
<213> ORGANISM: Unknown
<220> FEATURE:
<223> OTHER INFORMATION: Description of Unknown Organism: Primers -continued

```
<400> SEQUENCE: 5
tccagaattc catgaaagca ttctggggg                                      28

<210> SEQ ID NO 6
<211> LENGTH: 30
<212> TYPE: DNA
<213> ORGANISM: Unknown
<220> FEATURE:
<223> OTHER INFORMATION: Description of Unknown Organism: Primers

<400> SEQUENCE: 6
gttgaattca catgatgata ctgactgttg                                     30

<210> SEQ ID NO 7
<211> LENGTH: 30
<212> TYPE: DNA
<213> ORGANISM: Unknown
<220> FEATURE:
<223> OTHER INFORMATION: Description of Unknown Organism: Primers

<400> SEQUENCE: 7
ggtcctgggg tgattattta cggctgtggc                                     30

<210> SEQ ID NO 8
<211> LENGTH: 30
<212> TYPE: DNA
<213> ORGANISM: Unknown
<220> FEATURE:
<223> OTHER INFORMATION: Description of Unknown Organism: Primers

<400> SEQUENCE: 8
gtttaactca catgatgata ctgactgttg                                     30
```